(12) United States Patent
Najafi et al.

(10) Patent No.: US 7,393,522 B2
(45) Date of Patent: *Jul. 1, 2008

(54) PHYSIOLOGICALLY BALANCED, IONIZED, ACIDIC SOLUTION AND METHODOLOGY FOR USE IN WOUND HEALING

(75) Inventors: Ramin Najafi, Novato, CA (US); Lu Wang, Emeryville, CA (US); Mansour Bassiri, Davis, CA (US); Jane Yang, Emeryville, CA (US)

(73) Assignee: NovaBay Pharmaceuticals, Inc., Emeryville, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 10/655,493

(22) Filed: Sep. 3, 2003

(65) Prior Publication Data

US 2004/0137078 A1 Jul. 15, 2004

Related U.S. Application Data

(60) Continuation-in-part of application No. 10/209,681, filed on Jul. 30, 2002, which is a continuation-in-part of application No. 10/000,919, filed on Nov. 2, 2001, now abandoned, which is a division of application No. 09/482,159, filed on Jan. 12, 2000, now Pat. No. 6,426,066.

(51) Int. Cl.
*A61K 31/74* (2006.01)
*A61K 33/40* (2006.01)
*A61K 33/14* (2006.01)

(52) U.S. Cl. .............. 424/78.04; 424/78.06; 424/78.07; 424/613; 424/661

(58) Field of Classification Search .............. 424/78.04, 424/78.06, 78.07, 613, 661, 78.05
See application file for complete search history.

(56) References Cited

U.S. PATENT DOCUMENTS

| | | | |
|---|---|---|---|
| 4,908,215 A | 3/1990 | Perlman | |
| 4,965,554 A | 10/1990 | Darling | |
| 5,090,410 A | 2/1992 | Saper et al. | |
| 5,422,126 A | 6/1995 | Howarth et al. | |
| 5,427,667 A | 6/1995 | Bakhir et al. ............... | 204/260 |
| 5,622,848 A | 4/1997 | Morrow ...................... | 435/173 |
| 5,731,008 A | 3/1998 | Morrow ...................... | 424/613 |
| 5,759,489 A | 6/1998 | Miura et al. | |
| 5,790,036 A | 8/1998 | Fisher et al. | |
| 5,879,292 A | 3/1999 | Sternberg et al. | |
| 5,891,074 A | 4/1999 | Cesarczyk | |
| 6,174,419 B1 | 1/2001 | Akiyama | |
| 6,207,201 B1 | 3/2001 | Piacenza ..................... | 424/665 |
| 6,283,938 B1 | 9/2001 | McConnell | |
| 6,296,744 B1 | 10/2001 | Djeiranishvili et al. ...... | 204/263 |
| 6,315,719 B1 | 11/2001 | Rode et al. | |
| 6,333,054 B1 | 12/2001 | Rogozinski ................. | 424/661 |
| 6,426,066 B1 | 7/2002 | Najafi et al. .............. | 424/78.04 |
| 2002/0182262 A1 | 12/2002 | Selkon ........................ | 424/600 |
| 2004/0208940 A1 | 10/2004 | Selkon ........................ | 424/601 |

FOREIGN PATENT DOCUMENTS

| | | |
|---|---|---|
| WO | WO99/34652 | 7/1999 |
| WO | WO 2001/13926 A2 | 3/2001 |
| WO | WO 2001/17909 A1 | 3/2001 |
| WO | WO 2001/42143 A2 | 6/2001 |
| WO | WO 01/54704 | 8/2001 |
| WO | WO 2003/045446 A1 | 6/2003 |

OTHER PUBLICATIONS

Bruk, M.E., "Aids Treatment with Nonlethal Intravenous Ozone Solution", Bionet. Virology, (1995).

Hayashi, et al., "Successful Treatment of Mediastintis after Cardiovascular Surgery Using Electrolyzed Strong Acid Aqueous Solution", Artifical Organs, 21(1), pp. 39-42, (1997).

Horiba, N., et al., "Bactericidal Effect of Electrolyzed Neutral Water on Bacterial Isolated From Infected Root Canals", Oral Surg. Oral. Med. Oral. Pathol. Oral. Radiol. Endod., (1999), 87(1), pp. 83-87.

(Continued)

*Primary Examiner*—Brian Kwon
(74) *Attorney, Agent, or Firm*—Sam L. Nguyen

(57) ABSTRACT

Described herein is a physiologically-balanced, acidic solution. Typically the solution is prepared by a chemical reactions or by the electrolysis of a solution comprising a mixture of an inorganic salt to form a physiologically balanced solution. This invention also relates to methods for use of the solutions, including a specialized bandage which may be used in combination with the solutions, or optionally with other topically applied materials. A mixture of inorganic salts and, optionally minerals, is used in order to mimic the electrolyte concentration and mixture of body fluid in an isotonic state. The solution typically comprises of one halide salt of lithium, sodium, potassium, calcium, and other cations. Typically the halide is fluoride, chloride, bromide, or iodide, and most typically chloride. A typical electrolyzed solution of the present invention has a pH within the range of about 2 to about 5, an oxidation reduction potential within the range of about +600 mV to about +1200 mV, and hypohalous acid concentration in the range of about 10 ppm to about 200 ppm. The solution has bactericidal, fungicidal, and sporicidal properties. The composition of the invention is nontoxic and has antibacterial properties, and is useful in any application in which antimicrobial properties are desirable.

7 Claims, 6 Drawing Sheets

OTHER PUBLICATIONS

Inoue, Y. et al., "Trial of Electrolyzed Strong Acid Aqueous Solution Lavage in the Treatment of Peritonitis and Intraperitoneal Abscess", Artificial Organs, 21(1), pp. 28-31, (1997).

Iwasawa, A. and Nakamura, Y., "Bactericidal Effect of Acidic Electrolyzed Water-Comparison of Chemical Acidic Sodium Hydrochloride (NaOCI) Solution", J. Jap. Assoc. Infec. Diseases, 70(9), pp. 915-922 (1996).

Li, X.W. et al., "Preliminary Study of Mocrobicide Effect and it's Mechanism of Electrolyzed Oxidizing Water", Chinese J. Epidem., 17(2), pp. 95-98 (1996).

Miyamoto, M. et al., "Effectiveness of Acidic Oxidative Potential Water in Preventing Bacterial Infection in Islet Transplantation", Cell Transplant, Jul.-Aug. 1999; 8(4), pp. 405-411.

Nakagawar, et al., "Spectroscopic Characterization and the pH Dependence of Bactericidal Activity of the Aqueous Chlorine Solution", Analytical Sciences, vol. 14, No. 4, pp. 691-698.

Ovington, L.G., "Matrix Metalloproteases and Wound Healing", Podiatry Today, (Oct. 1998).

Sekiya, et al., "Treatment of Infectious Skin Defects or Ulcers with Electrolyzed Strong Acid Aqueous Solution", Artificial Organs, 21(1), pp. 32-38, (1997).

Selkon, J. et al., "Development of a new Antiseptic For Preparing Wound Beds", European Tissue Repair Society Symposium, (Nov. 2000), pp. 53-58.

Selkon, J.B. et al., "Evaluation of the Antimicrobial Activity of a new Super-Oxidized Water Sterilox.RTM. for the Disinfection of Endoscopes", J. Hosp. Infec., 41(1), pp. 59-70, (Jan. 1999).

Tanaka, H. et al., "Antimicrobial Activity of Superoxidized Water", J. Hosp. Infec., 41(1), pp. 59-70 (Jan. 1999).

Tanaka, N. et al., "The Cleaning and Disinfecting of Hemodialysis Equipment Using Electrolyzed Strong Acid Aqueous Solution", Artificial Organs, 23(4), pp. 303-309, (Apr. 1999).

Venkitanarayanan, K.S. et al., "Efficiency of Electrolyzed Oxidizing Water for Inactivating *Escherichia coli* O157:H7, *Samonella enteritidis,* and *Listeria monocytogenes*", Appl. & Env. Microbiol., 65(9), pp. 4276-4279 (Sep. 1999).

"Wound Healing Part III:Can ProCyte Strike Gold with Copper?", The Genesis Report, (Feb. 1993).

Sabra Chartrand, "A Badnage with a Microcontroller", NY Times, Apr. 1999.

"Bandage with Built-In-Sensor can Identify Bacteria", Daily University Science News, 2001.

"Smart Bandage, 'Sports Infection'", Health, Nov. 2001.

Annette Cary, "PNNL's new 'Smart Bandage' May Help Heal Chronic Wounds", Handford News, Mar. 2000.

"'Smart Bandage' Diagnosis Danger Before Infection Takes Hold", Nov. 2001.

"Bandage Diagnosis Dangerous Infections", Medical Textiles, Dec. 1, 2001.

Louis Trandel, "Small Pliable Humidity Sensor, with Special Reference to the Prevention of Decubitus Ulcers", J. Am Geriatr Soc., 1975, vol. 23(7), pp. 322-326.

Singer, Peter "Smart Bandage Detects Bacteria with Silicon Sensor. (Emerging Technologies). (Brief Article)", Semiconductor International, vol. 24, No. 14, pp. 10-11, Dec. 2001.

Sunnen, "The Utilization of Ozone for External Medical Applications", Journal of Advancements in Medicine, May 1998, vol. 1, No.3, pp. 14-174 (entire document).

H.D. Dakin, "On the use of Certain Antiseptic substances in the statement in the treatment of infected Wounds", Br. Med. Journal, pp. 318-320, (1915).

JP Heggers, et al., "Bactericidal and wound healing properties of sodium Hypochlorite Solutions: The 1991 Lindberg Award", J. Burn Care Rehablitation, 12(5): 420-424, (1991).

Kiura, et al., "Bactericidal activity of electrolyzed acid water from solution containing sodium chloride at low concentration, in comparison with that at high concentration", J. Microbiol. Methods, 49(3): 285-293, 2002.

Len et al., "Ultraviolet spectrophotometric characterization and bactericidal properties of electrolyzed oxidizing water as influenced by amperage and PH", J Food Prot., 63(11): 1534-1537, (2000).

Nagamatsu, et al., "Durability of bactericidal activity in electrolyzed neutal water by storage", Dent Mater J. 21(2): 93-104,. 2002.

Okubo, et al., "Cytotoxicity and microbicidal activity of electrolyzed strong acid water and acidic hypochlorite solution under isotonic conditions" 73(10): 1025-1031, (1999).

Shetty, et al., "Evaluation of microbicidal activity of a new disinfectant: Sterilox 2500 against Clostridium spores, Helicobacter pylori, vancomycin resistant Enterococcus species, Candida albicans and several Mycobacterium species", J. Hosp. Infec., 41(2): 101-105, (1999).

The Genesis Report "Wound Healing Part III: Can ProCyte Strike Gold with copper?", Online abstract, (1993).

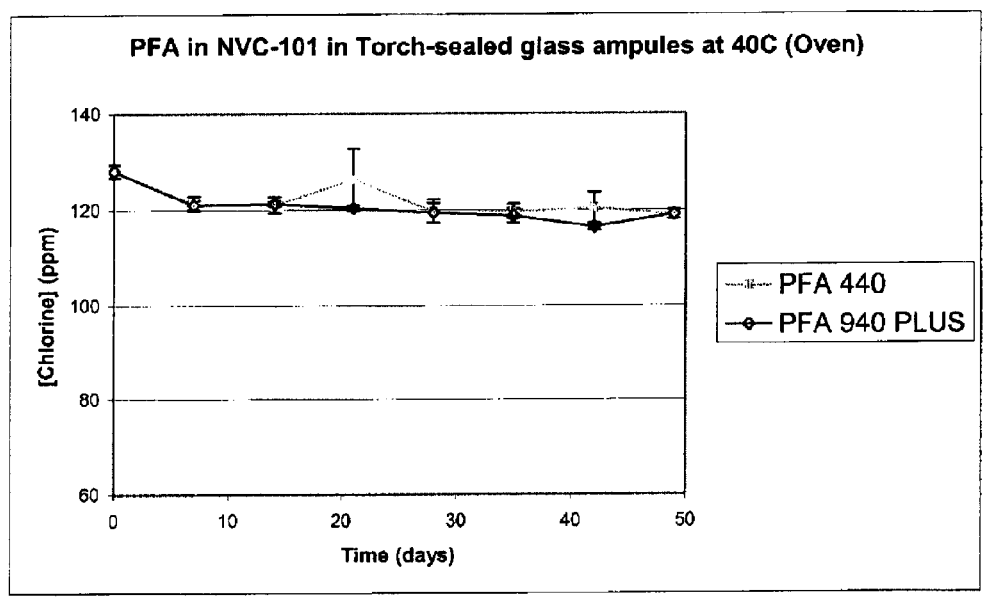
Figure 4: No reaction of HOCl or $Cl_2$ with PFA at 40 °C

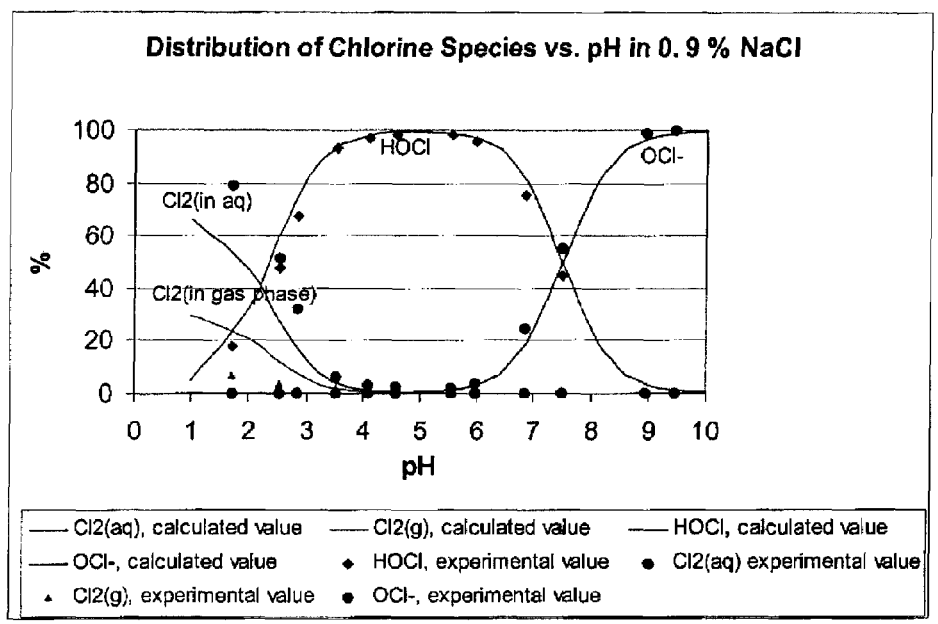
Figure 5: Distribution of Chlorine Species vs pH in 0.9% NaCl

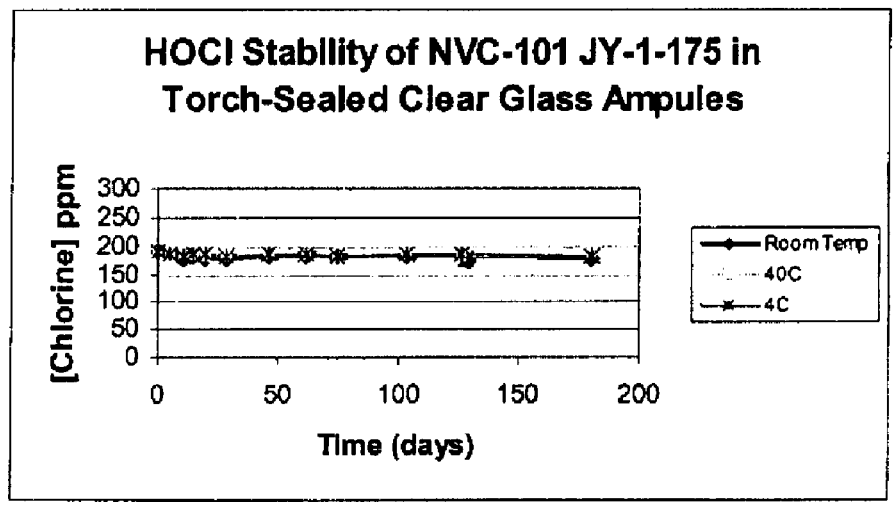
(a)
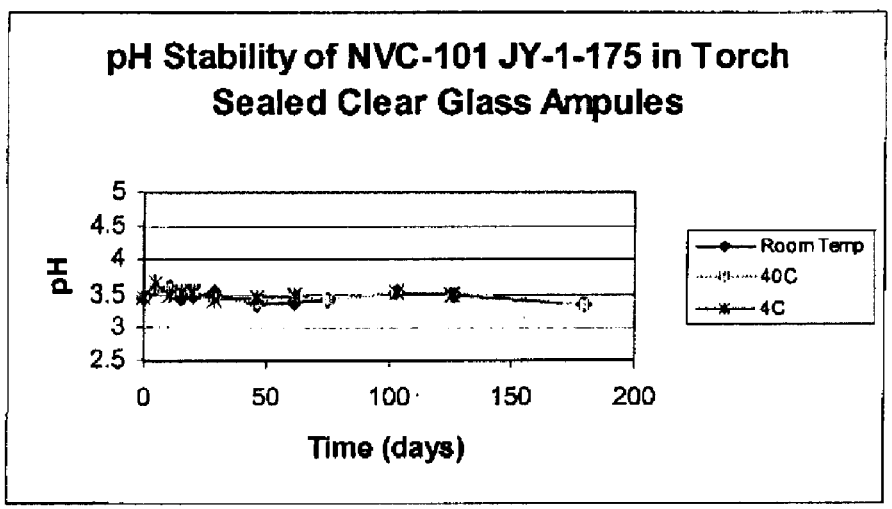
(b)
Figure 6: Stability of HOCl in 0.9 % saline at pH 3.5

PHYSIOLOGICALLY BALANCED, IONIZED, ACIDIC SOLUTION AND METHODOLOGY FOR USE IN WOUND HEALING

CROSS-REFERENCE TO RELATED APPLICATIONS

This application is a continuation-in-part of U.S. application Ser. No. 10/209,681, filed Jul. 30, 2002, which is a continuation-in-part of U.S. application Ser. No. 10/000,919, filed Nov. 2, 2001, now abandoned which is a divisional of U.S. patent application Ser. No. 09/482,159, filed Jan. 12, 2000, now U.S. Pat. No. 6,426,066 all of which are incorporated herein by reference in their entirety.

BACKGROUND OF THE INVENTION

1. Field of the Invention

This invention relates to a physiologically balanced, ionized, acidic solution that is useful in wound healing and other applications in which antimicrobial properties are desirable. The ionized solution may be prepared by electrolysis, i.e., it is an electrolyzed solution or by other methods including chemical or physical methods. The solution may also be prepared in situ. In addition, the invention relates to a methodology of using the solution of the invention, in a variety of applications, for example, a specialized bandage which may be used in combination with the solution or with other solutions or topically applied materials.

2. Brief Description of the Background Art

Various electrolyzed acidic salt solutions, their properties, and their uses have been described in the art. Several examples are provided below.

U.S. Pat. No. 5,622,848, issued Apr. 22, 1997, to Morrow, discloses a microbicidal solution for in vivo and in vitro treatment of microbial infections. The solution comprises an electrolyzed saline containing regulated amounts of ozone and active chlorine species, wherein the ozone content is between about 5 and 100 mg/L, the active chlorine species content is between about 5 and 300 ppm and a pH range from 7.2-7.6. The active chlorine species comprises free chlorine, hypochlorous acid, and the hypochlorite ion, as measured by a chlorine selective electrode. The solution is prepared by subjecting a 1% or less saline solution to electrolysis under conditions sufficient to produce the desired active ingredients. The solution is preferably utilized at an isotonic saline concentration, and may be adjusted with hypertonic saline. The solution may be used for in vitro treatment of infected whole blood, blood cells, or plasma to reduce contamination, and may be used in the treatment of fluids infected with HIV, hepatitis, and other viral, bacterial, and fungal agents. The solution may also be administered to warm-blooded animals, including humans, by intravenous injection or other modes, for similar purposes.

PCT publication No. WO9934652, published Jul. 8, 1999, of Marais, discloses the use of an electrochemically activated sodium hypochlorite-free irrigating medium to reduce the proliferation of bacteria and other microorganisms during tooth root canal. Anion- and cation-containing solutions are obtained by electrolysis of a 10% aqueous NaCl solution. The anion-containing solution is used at a pH of about 2-7 and an oxidation reduction potential (ORP) of about +1170 mV; the cation-containing solution is used at a pH of about 7-13 and an ORP of about −980 mV.

X. W. Li et al. (*Chinese J. Epidem.*, 17(2), pp. 95-98, 1996) reported a preliminary study of the microbicidal effect of electrolyzed oxidizing water. Electrolyzed oxidizing water was shown to completely kill *Staphylococcus aureus* and *Escherichia coli* within 15 seconds, while 10 minutes were required to completely kill all spores of *Bacillus subtilus* var. *niger*. Thirty seconds were needed to destroy the antigenicity of HBsAg. The oxidation reduction potential and pH values of electrolyzed oxidizing water were not significantly changed when stored for three weeks at room temperature under air-tight, light-free conditions.

A. Iwasawa et at. (*J. Jap. Assoc. Infec. Diseases*, 70(9), pp. 915-922, 1996) evaluated the bactericidal effect of acidic electrolyzed water on *S. aureus, S. epidermidis*, and *Pseudomonas aeruginosa*. At pH 5.0 to approximately 6.0, three bacterial strains were killed soon after being exposed to the acidic water containing 50 mg/L chloride, and the chloride concentration reportedly did not change after standing open for 6 hours. At pH 2.67 to approximately 2.80, the bactericidal effects were observed at a chloride concentration of 5 mg/L, and 80% of the chloride reportedly remained after standing open for 6 hours.

H. Tanaka et al. (*J. Hosp. Infect.*, 34(1), pp. 43-49, 1996) reported on the antimicrobial activity of superoxidized water. Superoxidized water is described as "a strong acidic and colorless solution with a high oxidation-reduction potential. The solution having an active chlorine concentration of 30 ppm, is prepared by mixing a small amount of salt with tap water in an electrolyser". The antimicrobial activity of superoxidized water was tested against methicillin-sensitive *S. aureus, Serratia marcescens, E. coli, P. aeruginosa*, and *Burkholderia* cepacia. The number of bacteria was reduced below the detection limit following incubation in superoxidized water for 10 seconds. The bactericidal activity of superoxidized water was similar to that of 80% ethanol, but superior to that of 0.1% chlorhexidine and 0.02% povidone iodine.

Y. Inoue et al. (Artificial Organs, 21(1), pp. 28-31, 1997) reported on the use of electrolyzed strong acid aqueous solution lavage in the treatment of peritonitis and intraperitoneal abscess. Peritoneal and abscess lavages were performed using an electrolyzed strong acid aqueous solution to treat seven patients with peritonitis and intraperitoneal abscesses. The period of irrigation in the seven patients ranged from 9 to 12 days, with conversion to microorganism negative state observed within 3 to 7 days. The authors describe the solution as being "acidic water that contains active oxygen and active chlorine and possesses a redox potential" and having an active chlorine concentration less than 50 ppm.

S. Sekiya et al. (*Artificial Organs*. 21(1), pp. 32-38, 1997) reported on the use of electrolyzed strong acid solutions in the treatment of infectious skin defects and ulcers using. The clinically applied therapy of electrolyzed strong acid aqueous solutions were found to be effective in the treatment of infectious ulcers. Sekiya et al. describe the strong aqueous solution (ESAAS) as being "generated by electrolyzing water and a small quantity of salt with a cation transfer filter."

H. Hayashi et al. (*Artificial Organs*, 21(1), pp. 39-42, 1997) reported on the use of electrolyzed strong acid aqueous solutions (ESAAS) in the treatment of mediastinitis following cardiovascular surgery. Hayashi et al. described ESMS as being "produced by electrolyzing sodium chloride solution. ( . . . ) ESAAS is produced by electrolyzing the sodium chloride solution using an ion-exchange membrane that separates the positive and negative electrodes. A small amount of sodium chloride is added to the water to facilitate electrolysis and increase the concentration of dissolved chloride." The solution is disclosed as having a pH less than 2.7, $Cl_2$ more than 30 ppm, ORP more than 1100, and dissolved $O_2$ of more than 20 ppm. The mediastinal wound was left open and irrigated with ESMS one to three times daily until the infection was eradicated. Satisfactory growth of granulation tissue was observed in all patients treated, with no evidence of adverse effects attributable to ESMS.

N. Tanaka et al. (*Artificial Organs*, 23(4), pp. 303-309, April 1999) reported on the use of electrolyzed strong acid aqueous solutions to clean and disinfect hemodialysis equipment. The solutions were found to directly inactivate bacterial endotoxins, and proved to be more economical than the conventional disinfecting method. The "electrolyzed strong acid aqueous solutions are disclosed to be "strongly acidic water which is made by electrolyzing tap water containing 500-1000 ppm salt (NaCl >99% pure) in a cell partitioned by a polyester diaphragm. It has an acidity of 2.3-2.7 pH, more than 1,000 mV in oxidation-reduction potential and 10-50 ppm in available chlorine."

J. B. Selkon et al. (*J. Hosp. Infec.*, 41(1), pp. 59-70, January 1999) evaluated the antimicrobial activity of a new superoxidized water, STERILOX® (Sterilox Medical Limited, 85 E Milton Park, Abingdon, Oxon OX14 4RY, UK) for the disinfection of endoscopes. This superoxidized water is prepared from a 35.7% NaCl in a 1 to 20 dilution, and is described as being "generated at the point of use by passing a saline solution over coated titanium electrodes at 9 amps. The product generated has a pH of 5.0-6.5 and an oxidation reduction potential of >950 mV." The antimicrobial activity of STERILOX® was tested against *Mycobacterium tuberculosis, M. avium-intracellulare, M. chelonae, E. coli* (including type 0157), *Enterococcus faecalis, P. aeruginosa, B. subtilus* var. *niger* spores, methicillin-resistant *S. aureus, Candida albicans*, poliovirus type 2, and human immunodeficiency virus HIV-1. Under clean conditions, freshly generated STERILOX® was found to be highly active against all these microorganisms, giving a 5 $\log_{10}$ (99.999%) or greater reduction in 2 minutes or less.

U.S. Pat. No. 6,296,744 assigned to Sterilox Technologies International Limited, discloses an apparatus for the electrochemical treatment of a liquid medium, which allows for the production of a sterilizing solution as well as the decontamination and purification of liquid mediums from toxic organic substances and other impurities. The process utilizes solution having an average salinity of 0.1 to 1.0 g/l and a chloride concentration of up to 50 mg/l, and the process is carried out using a current of 500 to 1000 mA with potential difference of 10-12 volts. The patent also discloses that the optimum pH parameters for anodically-treated water are 6-7, and for cathodically-treated water 8-9. However, the patent further discloses that the apparatus proposed aims to achieve solutions of active chlorine with a pH of between 4.5 and 7.5 used as a sterilizing solution, disinfectant, decontaminant, bleaching agent, detergent or medicine with antibacterial and antiviral action.

K. S. Venkitanarayanan et al. (*Appl. & Env. Microbiol.*, 65(9), pp. 4276-4279, September 1999) evaluated the efficacy of electrolyzed oxidizing water for inactivating *E. coli* 01 57:H7, *Salmonella enteritidis*, and Listelia monocytogenes. A five-strain mixture of *E. coli* 01 57:H7, *S. enteritidis*, or *L. monocytogenes* was inoculated in electrolyzed oxidizing water at various temperatures, for various time periods. The electrolyzed oxidizing water is produced from a saline base solution containing approximately 12% by weight. NaCl. The electrolyzed oxidizing water is also described as having a 0.1% salt, $Cl_2$ of 10-80 ppm, pH less than 2.7 as well as an electrolyzed oxidizing water having $Cl_2$ of 73-86 ppm, and pH of 2.38-2.48. At 4° C. and 23° C., an exposure time of 5 minutes, the population of all three pathogens in the treatment samples was reported to be reduced by approximately 7 log CFU/mL, with compete inactivation by 10 minutes of exposure. A reduction of greater than 7 log CFU/mL in the levels of the three pathogens was reported to occur in the treatment samples incubated for 1 minute at 45° C. or for 2 minutes at 35° C.

SUMMARY OF THE INVENTION

This invention relates to stable physiologically balanced, non-cytotoxic 10 ionized, acidic solutions and to a methodology for their use. The invention also relates to applications of the solutions of the invention, including a specialized bandage which may be used in combination with the solutions, or with other topically applied materials. The ionized solutions may be prepared by electrolysis. In another aspect of the invention, the solutions are prepared by chemical methods, including synthesis, or by mechanical methods such as by mixing, or are prepared in situ.

A novel physiologically balanced solution was recently disclosed in co-pending applications, U.S. application Ser. No. 10/209,681, filed Jul. 30, 2002, U.S. application Ser. No. 10/000,919, filed Nov. 2, 2001, and U.S. Ser. No. 09/482,159, filed on Jan. 12, 2000 (corresponding to WO 01/54704 A1 published on Aug. 2, 2001), all of which are incorporated herein by reference in their entirety.

The composition of the invention may be prepared using an inorganic salt in physiologically balanced form. The inorganic salt is used in order to mimic the electrolyte concentration and mixture of extra cellular body fluid in an isotonic state. The solution typically comprises the halide salt of sodium, or potassium, or calcium, and other cations. Typically the halide is fluoride, chloride, bromide, or iodide, and most typically chloride. In part, the concentrations of the salinity, the pH and the active chlorine concentration are such that they give the composition its unique properties.

The solutions of the present invention may be prepared using a single inorganic salt, forming an initial concentration of the salt in the aqueous solution of about 0.4 to about 1.0%. The halide-comprising salt may be selected from the group consisting of lithium halide, sodium halide, potassium halide, magnesium halide, calcium halide, zinc halide, cesium halide, rubidium halide and barium halide. Non-limiting examples of the inorganic salt may also include NaBr, NaI, NaF, LiBr, LICl, Lil, $Mgl_2$, $MgBr_2$, KI, KCl, KBr and the like. The inorganic salt may be a metal halide such as a chloride comprising salt selected from the group consisting of LiCl, NaCl, KCl, $MgCl_2$, $CaCl_2$, and $ZnCl_2$. In one aspect of the invention, the initial salt concentration used in the aqueous solution is about 0.4 to about 0.9%.

In another aspect of the invention, the inorganic salt is sodium chloride at a concentration of about 0.4 to about 1.0% NaCl which is about four-tenth to slightly higher than full strength of normal or isotonic saline solution. According to Parker's McGraw-Hill Dictionary of Scientific and Technical Terms, S. P. Parker, editor, Fifth Edition, "normal saline", "physiological saline", "physiological salt solution" are defined as a "solution of sodium chloride in purified water, containing 0.9 grams of sodium chloride in 100 milliliters; isotonic with body fluids." For different salts such as lithium halides, potassium halides, and the like, the concentration of the salt in solution making up an isotonic solution may differ from the concentration of sodium chloride in an aqueous solution in order to maintain the desired osmolarity of the solution of the invention. In yet another aspect of the invention, the sodium chloride in the aqueous solution is at a concentration of about 0.4 to about 0.9%.

In one aspect of the present invention, we have created a composition comprising a stable, physiologically balanced, noncytotoxic acidic solution, herein also referred to as the NVC-101 solution, where the starting solution prior to its preparation, for example, by electrolysis, comprises a total concentration of the halide-comprising salt ranging from about 0.4 g/L to about 16 g/L; more preferably ranging from about 4 g/L to about 10 g/L; and, most preferably, ranging from about 4 g/L to about 9 g/L. The solution may optionally contain minerals. The solution is adjusted to a pH within the range of about 2 to about 5, and has an oxidation reduction potential within the range of about +600 mV to about +1200 mV, and the solution having a total active halogen concentration of 0.1 to about 1,000 ppm, preferably from about 10 to about 200 ppm, and most preferably from about 40 to about 190 ppm. In one aspect of the invention, the active halogen is selected from the group consisting of fluorine, chlorine, bromine, and iodine. In another aspect of 10 the present invention, the halogen is chlorine.

The starting solution used to prepare the physiologically balanced, acidic composition of the invention may comprise a halide-comprising salt selected from the group consisting of lithium halide, sodium halide, potassium halide, magnesium halide, calcium halide, zinc halide, cesium halide, rubidium halide and barium halide. The composition of the salts of the solution of the present invention are physiologically balanced, as salt contents that are too low or too high in concentration relative to a physiological balanced solution may damage cells. The term "starting solution" is defined as the solution containing the added salt composition prior to any reaction or electrolysis of the solution.

In another aspect of the invention, the starting solution of the halide-comprising salt, and optionally containing minerals, is converted to an acidic water solution through electrolysis. The electrolyzed, halide-comprising solution has a typical oxidation reduction potential (ORP) of about +600 to +1200 mV. The pH of the electrolyzed, halide comprising solution, such as a chlorine-comprising solution, is typically lowered to about 5 or less, but not less than a pH of 2, preferably with a pH range of about 3.0 to 4.0, more preferably a pH of about 3.5 to 4.0, most preferably a pH of about 3.5, giving the solution virucidal, bactericidal, fungicidal, and sporicidal properties. The halide-comprising acidic solution is physiologically balanced. Typically the salts are supplied in the form of a halide-comprising salt which is ionized during electrolysis. These physiologically-balancing halide-comprising salts are selected from the group consisting of lithium halide, sodium halide, potassium halide, magnesium halide, zinc halide, lithium halide, barium halide, cesium halide, and rubidium halide. Preferably, these physiologically-balancing halide-comprising salts are selected from the group consisting of lithium halide, sodium halide, potassium halide, magnesium halide, zinc halide, lithium halide, and barium halide. Most preferably the salts are selected from sodium chloride, potassium chloride, magnesium chloride, or zinc chloride.

In another aspect of the invention, the starting solution for the preparation of 10 the electrolyzed solution comprises of at least one metal halide salt. Where more than one metal halide salts are present, the salts may be present in the same or different concentrations from each other.

In one exemplary solution of the present invention, the starting solution for the preparation of the electrolyzed solution includes sodium halide present at a concentration ranging from about 4.0 g/L to about 9.9 g/L. In one aspect of the invention, the halide is chloride.

A particularly preferred starting solution for preparation of the solution includes sodium chloride present at a concentration ranging from about 0.4 glL to about 14 g/L.

In one aspect of the invention, the solution of the invention may be prepared by electrolysis by subjecting the starting salt solution to electrolysis under conditions sufficient to produce the desired composition.

In another aspect of the invention, the salt comprising acidic solutions may be prepared by chemical methods, including chemical synthesis, or by physical methods such as mixing the components of the solution. In another aspect, the solution is prepared in situ at the location where it is to be applied or used directly. Methods for the preparation of the solution in situ are provided below.

The acidic solution of the invention contains hypohalous acid and may contain, among other components, hydroxyl free radicals, oxygen, and ozone. These components comprise some of the same oxidizing agents involved in physiological systems associated with wound healing and tissue repair and regeneration. For example, hypochlorous acid is the chief bactericidal agent produced by neutrophils at sites of inflammation, injury, and wounds.

Because the solutions of the invention are physiologically balanced, when applied to infected wounds, they enhance the process of healing substantially. Antimicrobial properties of the solutions of the inventions have been tested against many organisms, including *Escherichia coli, Listeria monocytogenes, Staphylococcus aureus*, methicillin-resistant *S. aureus* (MRSA), *Pseudomonas* aeruginosa, *Lactobacillus*, yeast, vancomycin-resistant *enterococcus*, molds, and spores, including spores of anthrax. In particular, the solutions of the present invention have been used to successfully treat three different strains of Baccifus anthracis. Vancomycin-resistant bacteria, MRSA, and others are easily destroyed by the solutions of the present invention. The solutions of the invention are osmotically balanced, environmentally friendly, and have minimal cytotoxicity. For example, no cytotoxicity was observed in rabbits' eyes nor in in vitro cytotoxicity studies carried out to date.

When the solution of invention is applied in in vitro studies to human skin cells: keratinocytes, fibroblasts and melanocytes, it is well tolerated and the minimal-cytotoxicity parallels that of sterile saline solution. The solution of invention was also applied in in vivo studies to rabbit eyes using the Draize test, which provides direct observations of the eyes' anatomical and physiological changes after exposure of the eyes to test solutions. In comparative studies, rabbits received randomly and in a double-blind fashion either saline (15 eyes) or the solutions of the present invention (15 eyes). Each eye received 0.1 ml of solution every 8 hours and observations were collected at various time points. The treated eyes were observed for ocular irritation. The cytotoxicity index was zero for both arms of the studies: saline and the solutions of the invention treated rabbits tolerated both treatments similarly, and did not show any irritation response. The isotonic solutions of the present invention were determined to be non-toxic to biological tissues and comparable to saline solutions.

In one aspect, the solution of the invention has the following stability characteristics. After the solution is stored in a container or storage medium for a period of about 25 months at about 4° C., the solution was determined to have a measured oxidation reduction potential (ORP) of no less than about 90% but not more than about 99.9%, preferably no less than about 95% but no more than about 99.9%, and most preferably no less than about 97.5% but not more than about 99.9% of the ORP of the solution freshly prepared prior to storage, while maintaining up to 5 logs of reduction in the activity of the microorganisms after 10 to 60 seconds of exposure to the solution.

The stable solutions prepared and stored in a medium according to the methods of the present invention have extended stability or shelf life characteristics, depending on the nature of the medium of storage, the temperature of storage, and whether the container or medium has been opened. For example, the solution may have a ORP of no less than 95% of the ORP of the freshly prepared solution for at least 24 months when stored at room temperature if the container has not been previously opened or used after storage. In one aspect, the stable solution of the present invention may be stored in a gas tight, sealed container which further extends the stability characteristics of the solution. In addition, the solutions of the present invention will have a longer storage shelf life if the solutions are stored below room temperature rather than when stored at or above room temperature. "Room temperature" is being defined herein as between 20 to 25° C.

As defined herein, "stability" of the solution or a "stable solution" means that the solution of the present invention maintains up to 5 logs of reduction in the activity of the microorganisms after 10 to 60 seconds of exposure to the solution.

The relative stability of the solution of the invention may also be determined from chemical analysis or by spectroscopy. The stability of the solution may be determined by iodometric titration or by UV-VIS for the presence of active halide as described herein.

A stable solution as defined in this invention is a solution prepared and stored according to the procedures described herein and having a reduced concentration of active chlorine over a period of time, preferably a reduction of between 1-95% of active chlorine species, more preferably a reduction of between 5-15% of active chlorine species, and most preferably a reduction of between 0-5% of active chlorine species in solution as determined by UV-VIS or iodometric titration over a period of at least one month, preferably at least 2 months and more 10 preferably, at least 3 months.

The measurement of the pH of a solution of the present invention is another complementary method for determining the stability of the solution in addition to the UV-VIS or iodometric titration method.

The concentration of "active chlorine" or "free chlorine" species as defined herein, refers to chlorine comprising species such as HOCl, NaOCl and $Cl_2$ present in a solution of this invention, and the total concentration of all of the active chlorine or free chlorine species in solution can be determined by UV-VIS or by iodometric titration. The active chlorine species in solution may also be expressed as $[HOCl]_{total}$ where $[HOCl]_{total}$ is defined as the sum of the concentration of HOCl, OCl$^-$, and $Cl_2$ in solution; that is, $[HOCl]_{total}=[HOCl]+[OCl^-]+[Cl_2]$. The concentration of active chlorine species may also be expressed in ppm, where the ppm concentration is equal to the number of mM of the species times the molecular weight of the particular species being measured. For example, if a concentration of $Cl_2$ is referred to in ppm unit, conversion to the concentration in mM requires that the concentration in ppm be divided by the molecular weight of $Cl_2$ (MW of 71).

Similarly, the concentration of the "active halogen" or "hypohalous acid" species refers to the concentration of the corresponding halogen containing species HOX, NaOX, or $X_2$ as discussed above, where X is a halogen atom.

The species HOCl, NaOCl and $Cl_2$ are equivalent in their reactions in the iodometric titration methods or as determined by the UV-VIS method as follows:

$HOCl+HCl \rightarrow Cl_2+H_2O$ $HOCl+NaOH \rightarrow NaOCl+H_2O$ $Cl_2+2NaOH \rightarrow NaOCl+NaCl+H_2O$ The active chlorine species in a solution may be measured by an iodometric titration method, by reacting the solution with KI and then titrating the solution with a $Na_2S_2O_3$ solution in the presence of starch. The reaction of the active chlorine species occurs as follows:

$HOCl+HCl+2KI \rightarrow I_2+2KCl+H_2O$ $Cl_2+2KI \rightarrow I_2+2KCl$ $2HCl+NaOCl+2KI \rightarrow I_2+2\ KCl+NaCl+H_2O$ $I_2+2Na_2S_2O_3 \rightarrow 2NaI+Na_2S_4O_6$ The active chlorine can also be reacted with NaOH and is converted to NaOCl.

NAOCl has an absorption at 292 nm with a known molar absorptivity of 362 $M^{-1} cm^{-1}$. Therefore, the concentration of the active chlorine species can be measured and is directly correlated with the concentration with any one of the species HOCl, NaOCl, or $Cl_2$ or with the combination of these species in a 1:1 basis.

Similarly, the concentration of a hypohalous acid species in solution as defined herein correspond to the concentration of the active bromine or free bromine, active iodine or free iodine, and active fluorine, or free fluorine species in the solution as defined above.

In one aspect, the solution of the invention has the following reduced cytotoxicity. When the solution of invention is applied in in vitro studies to human skin cells such as keratinocytes, fibroblasts and melanocytes, it is well tolerated and no substantial cytotoxicity was measured using Tripan Blue intergen detection and pro check cell viability assay. In another aspect, the solution of the present invention exhibits the minimal-cytotoxicity parallels to that of sterile saline solution.

Without being bound by any theory offered herein, it is believed that the minimal cytotoxicity of the solution of the present invention depends on the concentration of OCl$^-$ in the solution as disclosed herein.

Because the composition of the present invention is non-toxic and has antibacterial properties it is useful in any application in which antimicrobial properties are desirable. Such applications include, without limitation, treatment of wounds, burns, and canker sores; irrigation; cleaning of tissue sites (e.g., pre and post-operative); ophthalmic applications (e.g., in contact lens cleaning solutions or for irrigation of the eye before, during, or post ophthalmic surgery); for dermatological applications, psoriasis; and numerous applications which are readily apparent to one skilled in the art. Unlike many other inorganic halide solutions used in similar applications, the composition of the invention has minimal to no side effects. For example, in Draize testing in Rabbit eyes, when compared to other antiseptic solutions, the physiologically balanced, stable, acidic solution of the present invention behaves in a manner similar to saline solution.

In another Draize test, rabbit's eyes were treated with the solution of invention and compared with the ophthalmic grade Betadine (manufactured by: Alcon Co., TX, at a 5% concentration). Each eye received 0.1 ml of solution every 8 hours and observations were recorded at various time points. The Draize method relies on direct observations of the eyes' anatomical and physiological changes after exposure of the eyes to test solutions. Rabbits treated with the solution of invention tolerated the treatment without any signs of irritations, whereas, rabbits treated with ophthalmic grade Betadine did not tolerate the treatment and showed significant level of redness, ocular irritation and discomfort.

The composition of the invention can be incorporated into a variety of applications, including a bandage or wound dressing, as described subsequently herein. The physiologically balanced, acidic solution may be used in combination with a specially designed bandage in a wound treatment protocol as described subsequently herein. The specialized bandage includes an opening or "window" through which topical treatment materials such as the solution of the present invention may be applied.

Also disclosed herein is an article of manufacture comprising the composition of the invention packaged in a container. Surfaces of the container which are in contact with the composition of the invention are made of material which is not reactive with an oxidizing agent.

BRIEF DESCRIPTION OF THE DRAWINGS

FIG. 4 represents PFA in NVC-101 in Torch-sealed glass ampules at 40C (Oven).

FIG. 5 represents a distribution of Chlorine Species vs pH in 0.9% NaCl.

FIG. 6a represents a HOCl Stability of NVC-101 JY-1-175 in Torch-Sealed Clear Glass Ampules.

FIG. 6b represents a pH Stability of NVC-101 JY-1-175 in Torch Sealed Clear Glass Ampules.

DETAILED DESCRIPTION OF THE INVENTION

Figure 1:
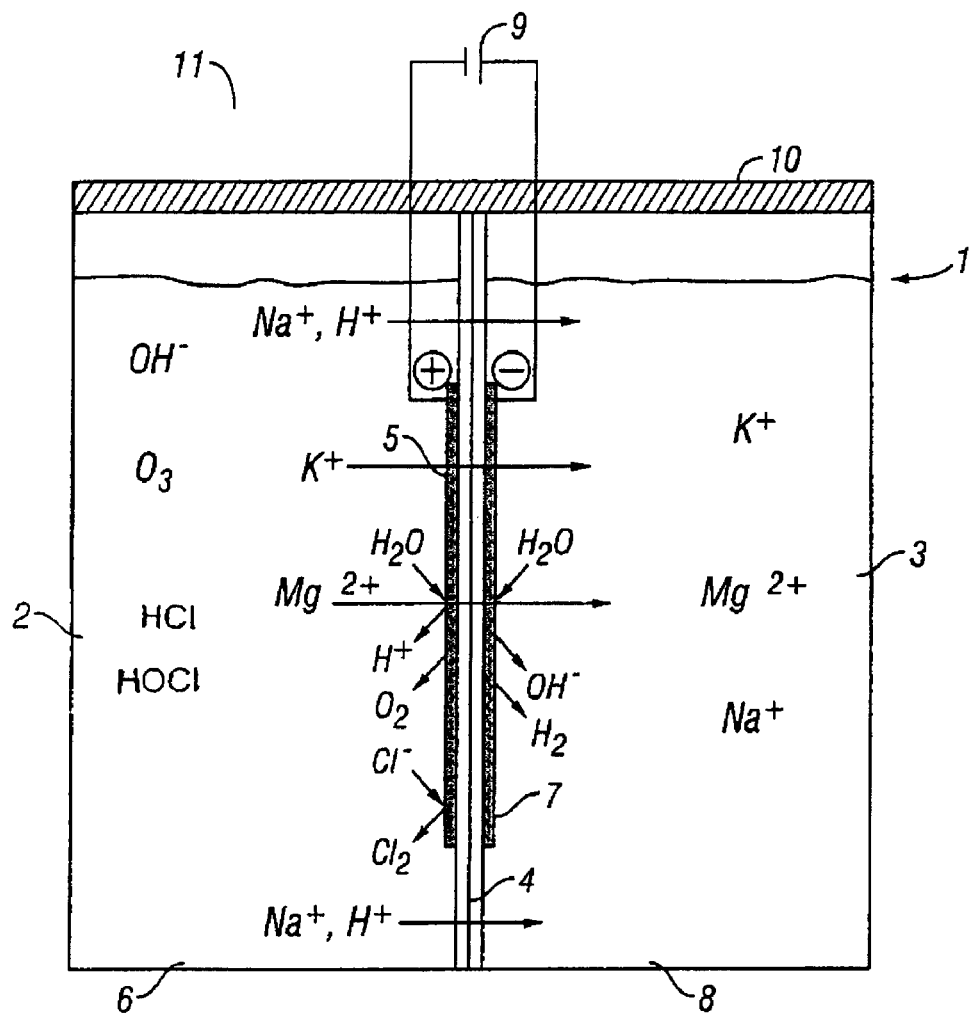
FIG. 1 is a cross-sectional schematic of an electrolyzing unit 1 having two compartments, identified in FIG. 1 as elements 2 and 3. Compartments 2 and 3 are separated by a semipermeable membrane 4. A positive electrode 5 is located in compartment 2, where a strong acidic solution 6 is generated. A negative electrode 7 is located in compartment 3, where an alkaline solution 8 is generated. Electrodes 5 and 7 are connected to a power source 9 which generates a current across semipermeable membrane 4. A lid 10 keeps electrolyzing unit 1 free from ambient air 11.

Described herein are stable, physiologically balanced, acidic solutions; methods and apparatus used in the production of the solution; methods for use of the solution, including the description of a specialized bandage for administering the solution or other topically applied treatment materials. Also disclosed are recommended packaging for the solution.

I. The Composition of the Invention

The present invention is a physiologically balanced, acidic solution, which may be generated from a starting solution comprising a total concentration of one halide-comprising salt ranging in osmolarty from about 0.014 to 0.547 osmol; more preferably ranging from about 0.123 to 0.376 osmol; and most preferably ranging from about 0.137 to 0.342 osmol. Optionally, minerals may be added, depending on the end use application.

A typical starting solution, prior to electrolysis, by way of example and not by way of limitation, may comprise of one chloride comprising salt selected from the group consisting of lithium chloride, sodium chloride, potassium chloride, magnesium chloride, calcium chloride, zinc chloride, cesium chloride, rubidium chloride, and barium chloride.

Representative concentration ranges for the various chlorine-comprsing salts that may be used in the starting solutions used to prepare solution are presented in Table 1, below.

TABLE 1

Compositions of Chloride Containing Salts In Preferred Embodiment Starting Solutions For Preparation Of An Acidic Solution

| Solution | Salt | MW (g/mole) | Preferred Ranges (g/L) | More Preferred Ranges (g/L) | Most Preferred Ranges (g/L) |
|---|---|---|---|---|---|
| 1 | NaCl | 58.50 | 0.400 to 16.000 | 3.600 to 11.000 | 4.000 to 10.000 |
|   |   | moles → | 0.007 to 0.274 | 0.062 to 0.188 | 0.068 to 0.171 |
|   |   | osmoles → | 0.014 to 0.547 | 0.123 to 0.376 | 0.137 to 0.342 |
| 2 | KCl | 74.59 | 0.510 to 20.401 | 4.590 to 14.025 | 5.100 to 12.750 |
|   |   | moles → | 0.007 to 0.274 | 0.062 to 0.188 | 0.068 to 0.171 |
|   |   | osmoles → | 0.014 to 0.547 | 0.123 to 0.376 | 0.137 to 0.342 |
| 3 | $MgCl_2$ | 95.30 | 0.434 to 17.377 | 3.910 to 11.946 | 4.344 to 10.860 |
|   |   | moles → | 0.005 to 0.182 | 0.041 to 0.125 | 0.046 to 0.114 |
|   |   | osmoles → | 0.014 to 0.547 | 0.123 to 0.376 | 0.137 to 0.342 |

Definition of Osmolarity: A 1 M solution of a non-dissociable solute is 1 Osmolar. (The solution contains $6.023 \times 10E23$ particles per liter). The solution of dissociable salt is n Osmolar, where n is the number of ions produced per molecules. Thus a 0.03 M solution of KCl is 0.06 Osmolar. (Irwin H. Segel, Biochemical Calculations, 2nd edition. Published by John Wiley & Sons, New York). Osmolarity is often considered in physiological studies where tissue or cells must be bathed in a solution of the same osmolarity as the cytoplasm in order to prevent the uptake or release of water. Blood plasma is 0.308 Osmolar. Thus the red blood cells suspended in a 0.308 Osmolar NaCl solution (0.154 M) would neither shrink nor swell. The 0.154 M NaCl solution is said to be isotonic with respect to the red blood cells (Irwin H. Segel et al).

The properties of the physiologically balanced, acidic solutions produced from the Starting Solutions described in Table 1 are presented in Table 2, below.

TABLE 2

Properties of Preferred Physiologically-Balanced Acidic Solutions Generated From NaCl Starting Solution Listed in Table 1

| | Preferred | More Preferred | Most Preferred |
|---|---|---|---|
| ORP (mV) | +600 to +1200 | +800 to +1190 | +1000 to +1180 |
| pH | 2.0–6.0 | 2.2–5.5 | 2.4–5.0 |
| Hypochlorous Acid Conc. (ppm) | 0.1–1000 | 1–200 | 60–190 |
| Molar Ratio[1] range of OCl⁻ over sum of OCl- and HOCl at 20° C. (%) | about 0–2.55 | about 0–0.82 | about 0–0.26 |

[1]Geo. Clifford White: Handbook of Chlorination and Alternative Disinfectants, page 218, 4th ed., John Wiley & Sons, Inc. New York, 1999.

II. Apparatus and Method for Making the Physiologically Balanced, Electrolyzed, Acidic Wound Healing Solutions The physiologically-balanced, acidic solution of the invention may be prepared using electrolysis. Electrolysis of water is the process by which the hydrogen ions are reduced, providing hydrogen gas, and the hydroxide ions are oxidized, providing oxygen gas.

The wound healing solution described herein was prepared using a SUNTRON® MWB-2 model electrolyzing unit of the kind manufactured by Koshin Co. Ltd., Kyoto, Japan. Equivalent wound healing solutions can be prepared using a SUPER OXSEED LABO® electrolyzing unit of the kind manufactured by ARV Co., Japan.

With reference to FIG. 1, which shows a general schematic of an electrolyzing unit in which a physiologically balanced, electrolyzed, acidic wound healing solution is prepared, and with reference to the SUNTRON® MWB-2 model electrolyzer, the electrolyzing unit 1 has a first compartment 2 and a second compartment 3, each of which have a capacity of about 3 liters. Compartments 2 and 3 are separated by a semi-permeable membrane 4. In the first compartment 2, a positive electrode 5 is located. In the first compartment 2 a strong acidic solution 6 is generated. In the second compartment 3, a negative electrode 7 is located. In the compartment 3, an alkaline solution 8 is generated. Electrodes 5 and 7 are connected to a power source 9 which generates a 0.9 A, 100V current. A lid 10 keeps the electrolysis unit free from contamination by ambient air 11.

13.5 g of Sodium chloride (Non-iodated, Morton) was added to 2.5 liters of distilled water to form a 5.38 g/liter or a 0.538% solution. 2.5 L of the solution was placed in first compartment 2 and 2.5 L of solution was placed in second Compartment 3. The power source 9, shown in FIG. 1, was turned on and power was applied for 15 minutes. The electrolysis was carried out at room temperature (about 25° C. to 30° C.), with no external heat added and no heat removed.

Salt solutions allow currents to pass between the electrodes, accelerating the process of electrolysis. The amount of salt necessary to affect the electrolysis process is minimal. During the electrolysis process, a halide salt, such as sodium chloride is in ionized form, as shown below.

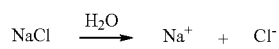

During electrolysis of saline, the sodium ions are attracted to the negatively charged electrodes, and will counterbalance the hydroxide ions on the alkaline side; the chloride ions travel to the positive electrode. The chloride ions then undergo an oxidative process which results in the generation of small quantities of chlorine gas that are immediately consumed to form hypochlorous acid, as illustrated below.

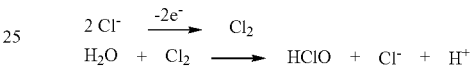

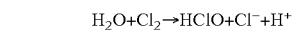

Chlorine species are in the form of HClO, ClO⁻, or Cl⁻; the balance among these ions is greatly affected by the pH of the solution. Without being bound by any theory, it is believed that HClO and ClO⁻ ions are effective sterilizing agents, with HClO being ten times more effective than ClO⁻. In acidic pH, most of the ClO⁻ ions are in the form of HClO.

Other halide salts undergoing electrolysis participate in similar ionization processes are well known and documented in the art.

An example of a typical physiological-balanced acidic solution of the invention has a concentration of sodium chloride ranging from about 0.5 to 9.9 g/L.

In one aspect of the invention, the concentration of hypohalous acid (HOX) in the solution is from about 0.1 to about 1,000 ppm, more preferably from about 1 to about 750 ppm, and most preferably from about 5 to about 500 ppm.

In one aspect of the invention the physiologically-balanced, electrolyzed acidic solution of the invention has a concentration of sodium cations ranging from about 0.01 g/L to about 7 g/L.

A typical physiologically-balanced, electrolyzed acidic solution produced using the starting materials described the invention has a low pH (about 2 to about 5), and an HClO concentration of about 0.1 ppm to about 1000 ppm. In one aspect of the invention, the pH range of the solution is 2.4 to 5.0. This combination of chemicals gives the electrolyzed acidic saline solution of the invention its superior antiseptic ability and its extended stability properties. In addition, the solution is characterized by remaining stable and active when stored for at least three months at room temperature.

A typical physiologically balanced solution of the invention is characterized by an oxidation reduction potential (ORP) from about +600 mV to about +1200 mV.

Standard electrolysis equipment, including the particular apparatus named herein, can be used in the manufacture of the electrolyzed salt solutions of the invention, as previously mentioned.

III. Chemical Processes for Preparing the Physiologically Balanced, Acidic Solutions Various chemical processes for the preparation of aqueous solution of hypochlorous acid are known in the art. For example, see The Merck Index, Tenth Edition M. Windholz, Ed., Merck & Co., Rahway, USA, 1983 and references cited therein. More generally, non-limiting examples of processes for the preparation of the solution of the present invention are provided in the following Reaction Scheme:

Reaction Scheme $$XOY + (Z-H-Z')_n \longrightarrow (HOY)_{n'} + (ZXZ')_{n''}$$

H = Hydrogen $\begin{bmatrix} Y = F, Cl, Br, I \\ X = Na, Li, K \end{bmatrix}$    $Z = \text{--}$    $Y = F, Cl, Br, I$    $Z = \text{--}$ $Z' = F, Cl, Br, I$    $n' = 1$    $X = Na, Li, K$ $n = 1$      $Z' = F, Cl, Br, I$ $n'' = 1$ $\begin{bmatrix} Y = F, Cl, Br, I \\ X = Na, Li, K \end{bmatrix}$    $Z = SO_4, CO_3, HPO_4$    $Y = F, Cl, Br, I$    $Z = SO_4, CO_3, HPO_4$ $Z' = Li, Na, K$    $n' = 1$    $X = Li, Na, K$ $n = 1$      $Z' = Li, Na, K$ $n'' = 1$

---

$Z = \text{--}$    $Y = F, Cl, Br, I$    $Z = \text{--}$ $Z' = F, Cl, Br, I$    $n' = 2$    $X = Na, Li, K$ $\begin{bmatrix} X(OY)_2 \\ X = Ca, Mg, Be \\ Y = F, Cl, I, Br \end{bmatrix}$    $n = 2$      $Z' = F, Cl, Br, I$ $n'' = 2$ $Z = SO_4, CO_3, HPO_4$    $Y = F, Cl, Br, I$    $Z = \text{--}$ $Z' = Li, Na, K$    $n' = 2$    $X = Ca, Mg, Be$ $n = 2$      $Z' = SO_4, CO_3, HPO_4$ $n'' = 1$ Non-limiting examples of processes for the preparation of the aqueous solutions of the present invention are provided as follows:

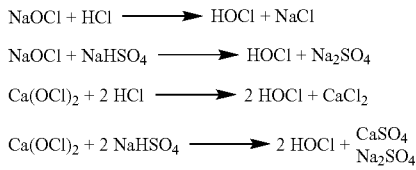

In each of the above representative processes for the preparation of the solution, upon the formation of the desired solution of the invention, the pH of the solution may be adjusted to the desired pH using standard methods known in the art for adjusting the pH of aqueous solutions.

In one aspect of the invention, the relative concentrations of reactants that will yield the composition of the stable aqueous physiologically balanced solutions of the present invention will vary according to the nature and type of reactants used to form the desired solutions. For example, the concentration of the salts comprising the solution of the invention may include the concentration ranges as disclosed in Table 1, In one aspect of the invention, the stable aqueous physiologically balanced solution of the present invention may also be prepared by the mixing of the appropriate starting chemicals immediately before using the solution.

In another aspect of the invention, the stable aqueous physiologically balanced solution of the present invention may also be prepared in situ by mixing the chemicals immediately before use. In situ mixing of the starting materials may be performed using various known methods in the art. For example, starting materials or reagents for the preparation of the composition of the invention may be separately stored, encased or contained in glass beads, ampules and the like, and the reagents can be admixed when the individual containers or beads encasing the reagents are released and allowed to react at the desired site for applying the solution. Where the reagents are contained in glass beads, ampules or the like, means for binding or holding the individual containers together, while allowing the release of the reactive components of the solution, may be accomplished to prevent the release of the containers at the desired treatment site.

Following manufacture, the solutions of the invention must be stored for use. Methods and materials of packaging are very important in maintaining and extending the useful shelf life of the solutions. For example, the surfaces of the containers which make contact with the solution should be made of a material which tends not to react with oxidizing agents.

We evaluated a number of different container materials, and surprisingly discovered that while a glass contacting surface preserves the long term strength (potency) of the solution, certain plastic surfaces or materials are not compatible with the solution for long term storage. By way of example and not by way of limitation, chemically resistant, coated soda lime amber glass 1 L or 500 mL bottles (manufactured by Lawson Mardon Wheaton, Miliville, N.J. 08332), meeting the requirements for Type III as established by the United States Pharmacopoeia, Volume XXIII (1995), and supplements thereto, under "Chapter <661>, Chemical Resistance-Glass Containers" make excellent storage containers for the physiologically-balanced solutions of the present invention. These bottles also meet the requirements for light protection established by the USP under Chapter <661>, "Light Transmission", which may be helpful in some instances. The bottle cap is fabricated from phenolic, and has a liner facing made out of TEFLON® (PTFE) which is less reactive than phenolic, and which helps seal the cap, preventing the passage of ambient air into the bottle. This bottle is available from AllPak Corp., Bridgeville, Pa.

A white (clear) glass bottle produced by the same manufacturer (AllPak Corp.), but absent the amber coloring also functions well in maintaining the stability of the solution. In one aspect of the invention, a gas tight sealing of the solution storage container preserves or extends the stability characteristics of the solution. Gas tight sealing methods employed for the storage, sealing and resealing of the containers after used may include methods known in the art such as using air tight screw caps, air tight lids, caps or lids having chemical resistant O-rings or gaskets, the use of sealing tapes, such as electrical tapes, or related methods known in the art for the airtight sealing or resealing of containers.

$Cl_2$ and HOCl are known as strong oxidants, and these species are known to react with many different synthetic plastic materials. An appropriate non-glass packaging material for the NVC-101 solution should be non-reactive to both $Cl_2$ and HOCl, and also not permeable to the species of the NVC-101 solution. We have studied the stability of HOCl at pH 3.5 in PET bottle, Barex bottle (British Petroleum), LDPE bottle, high density polyethylene bottle, polypropylene bottle, PFA bottle (Saville Corporation), Eastman Plastics bottle, PVC bottle and Pouch (white poly, foil, special high chemical resistant adhesive). In order to test if there are reactions of the materials with HOCl or $Cl_2$, the materials were cut into small pieces (about 1 gram strips) and sealed in the 30 mL ampules with the HOCl solutions (about 25 ml) at pH 3.5. The results show that among all of the above materials tested, PFA, a type of Teflon material, is the only material tested that does not react with HOCl or $Cl_2$ in the NVC-101 solution under these conditions (FIG. 4). Therefore, PFA can be used as the packaging material for the NVC-101 solution.

As defined herein, container materials or compositions that may be used for the storage of the NVC-101 solutions are considered to be "non-reactive", "does not react", "not permeable", are "chemically non-reactive", or are "resistant to oxidative degradation" are materials that are resistant to react with the NVC-101 solution and allow long term storage of the solution without adversely affecting the stability of the solution.

TABLE 3

Preparation of Solution 1 in Table 1 using a Synthetic Method (0.9% salt solution)[a]

| Reagent | MW (g/mole) | Weight (g) | mmoles | Volume (mL) | Molarity (moles/liter) |
|---|---|---|---|---|---|
| $H_2O$ | 18 | | | ~494.7 | |
| NaCl | | 4.34 | | | |
| NaOCl | 74.5 | 1.8 | 1.3 | 1.60 | 0.805 |
| HCl | 36.5 | 3.7 | 3.7 | 3.7 | 1 |

[a]See the Procedure #1 for the preparation of the 0.9% salt solution.

Stability of Hypochlorous Acid in 0.9% Saline Solution:

The decomposition of a mixture of hypochlorous acid and sodium hypochlorite was studied by Chapin from pH 1 to pH 13 in 1934. Chapin, R. M. J. Am. Chem. Soc. 1934, 56, 2211-2215. Chapin found a maximum decomposition rate in the neutral pH range. The following stoichiometry and rate expression was found to approximate the experimental observations:

$$2HOCl + OCl^- \rightarrow ClO_3^- + 2H^+ + 2Cl^-$$  Eq. 1

$$-d[HOCl]/3dt = k[HOCl]^2[OCl^-]$$  Eq. 2

The decomposition was also studied by Yokoyama and Takayasu in the neutral pH range. See Yokoyama, T.; Takayasu, O. Kogyo Kagaku Zasshi 1967, 70, 1619-1624. Their work was carried out in 0.8-4.6 M chloride ion to control the ionic strength, and no buffer was used. The authors proposed Eq. 3 as the rate expression based on their results, where a and b are constants.

$$-d[HOCl]/3dt = a[HOCl]^2[OCl^-]/(1+b[OCl^-])$$  Eq. 3

A more detailed study of the decomposition of hypochlorous acid from pH 5.0 to pH 8.0 was reported by Adam and co-workers. See Adam, L. C.; Fabian, I.; Suzuki, I., Gordon, G. Inorg. Chem. 1992, 31, 3534-3541. Under these conditions, they found that hypochlorous acid has a maximum decomposition rate at pH 6.89. The overall stoichiometry of decomposition of hypochlorous acid and hypochlorite ion (HOCl+OCl—) in the neutral pH region was determined as shown in Eq. 4.

$$xHOCl + (3-x)OCl^- \leftrightarrows ClO_3^{-+2}Cl^- + xH+$$  Eq. 4

A mechanism (Eq. 5-10) for the decomposition was proposed by these authors, in which $Cl_2O \cdot H_2O$ is formed as an intermediate.

$$2HOCl \leftrightarrows Cl_2O \cdot H_2O$$  Eq. 5

$$OCl^- + Cl_2O \cdot H_2O \rightarrow HOCl + HCl_2O_2^- \quad k_2 = 3.0 \text{ M}^{-1}\text{s}^{-1} \text{ (50° C.)}$$  Eq. 6

$$HCl_2O_2^- \leftrightarrows HClO_2 + Cl^-$$  Eq. 7

$$HOCl + Cl_2O \cdot H_2O \rightarrow HOCl + H_2Cl_2O_2 \quad k_2 = 3.6 \times 10^{-3} \text{ M}^{-1}\text{s}^{-1} \text{ (50° C.)}$$  Eq. 8

$$H_2Cl_2O_2 \leftrightarrows HClO_2 + Cl^- + H^+$$  Eq. 9

$$HOCl + HCl \leftrightarrows Cl_2 + H_2O$$  Eq. 10

Above pH 6, the step in Eq. 6 is the rate determining step. Below pH 6, Eq. 8 becomes the rate determining step. This step is very slow. The $k_2$ and $k_2$ values determined by Adam et al show that the reaction of $Cl_2O \cdot H_2O$ with $OCl^-$ is nearly 1000 times faster than with HOCl, suggesting that HOCl is much more stable in the acidic condition than in the neutral pH region. However, as the pH becomes acidic (pH<3), HOCl is converted rapidly to $Cl_2$ in the present of $Cl^-$ (Eq. 10), which is generated from HOCl self-decomposition (Eq. 5-10).

Synthesis of HOCl: In general, HOCl solutions were prepared by acidifying a NaOCl solution with HCl. The concentration of HOCl was determined by either Iodometric titration with Hatch solution or UV-VIS method. For analysis by UV-VIS method, aliquot of HOCl solution was converted to $OCl^-$ ($\epsilon=362$ $M^{-1}cm^{-1}$ @ 292 nm; see Furman, C. F.; Margerum, D. W. Inorg. Chem. 1998, 37, 4321) with 0.1 M NaOH solution. A Beckman pH meter was used to measure the pH of the solution. Distribution of Chlorine Species vs. pH in 0.9% Saline: The studies of Chapin, R. M., Yokoyama, T.; Takayasu, O., and Adam, L. C. et al show that the decomposition of HOCl to give inorganic ions $ClO_3^-$ and $Cl^-$ is slow in acidic condition. However, decomposition of HOCl may also occur via the formation of $Cl_2$ gas in the presence of excess NaCl (Adam, L. C. et al, 1992). The NVC-101 solutions as prepared according to a procedure described herein contains HOCl, 0.9% NaCl (0.155 M), and has a pH of about 3.5. Equations 11-14 show the equilibria existing in NVC-101 solution.

$HOCl \rightleftharpoons H^+ + OCl^-$  pKa =7.5  Eq. 11

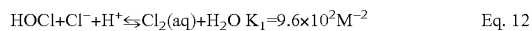

$HOCl + Cl^- + H^+ \rightleftharpoons Cl_2(aq) + H_2O$  $K_1=9.6\times10^2 M^{-2}$  Eq. 12

$Cl_2(aq) + Cl^- \rightleftharpoons Cl_3^-$  $K_2=0.18$ $M^{-1}$  Eq. 13

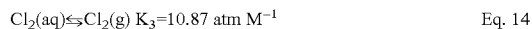

$Cl_2(aq) \rightleftharpoons Cl_2(g)$  $K_3=10.87$ atm $M^{-1}$  Eq. 14

The pKa of HOCl is 7.5. See Gerrisen, C. M.; Margerum, D, W. Inorg. Chem. 1990, 29, 2758-2762. At pH 3.5, hypochlorite exists predominantly as its conjugate acid form. At pH 7.5, $[HOCl]/[OCl^-]=1:1$. As shown in Eq. 12, high 1s acidity (or higher concentrations of $H^+$) favors the formation of $Cl_2$. See Wang, T. X.; Margerum, D. W. Inorg. Chem. 1994, 33,1050-1055. As the concentration of $Cl_2$ is increased in the solution, the formed $Cl_2$ may equilibrate to gaseous chlorine and is liberated to the headspace of a container (Eq. 14). Therefore, degassing of $Cl_2$ to the head space may become a major path for decreasing the concentration of HOCl at low pH in 0.9% NaCl solution in storage containers with large a headspace.

The distribution of chlorine species over a pH range in a 0.9% NaCl is shown in FIG. 5. The Figure shows the specific pH ranges wherein $Cl_2$ concentrations may be minimized. The chlorine species distribution curves (% vs pH) in FIG. 5 were calculated based on the pKa, $K_1$, $K_2$ and $K_3$ values available from literature. See Gerrisen, C. M.; Margerum, D, W. Inorg. Chem. 1990, 29, 2758-2762; Wang, T. X.; Margerum, D. W. Inorg. Chem. 1994, 33,1050-1055; Wang, T. X.; Kelly, M. D.; Cooper, J. N.; Beckwith, R. C. Margerum, D. W. Inorg. Chem. 1994, 33, 5872-5878; and Bartlett, W. B.; Margerum, D. W. Environ. Sci. Technol. 1999, 33, 3410-3414. The calculation results were verified by experiments. The experiments were carried out by using multiple wavelengths method, in which the molar absorptivities of HOCl, $Cl_2(aq)$, and $Cl_3^-$ are at wavelengths 220, 232, and 325 nm. The absorbances at these wavelengths were used to set three equations according to Eq. 15:

$A=\epsilon^{HOCl}[HOCl]+\epsilon^{Cl3-}[Cl_3^-]+\epsilon^{Cl2}[Cl_2]$  Eq. 15

The molar absorptivities used in this study are listed in Table 4.

TABLE 4

| Wavelength nm | $\epsilon^{HOCl}$ $M^{-1}cm^{-1}$ | $\epsilon^{Cl2}$ $M^{-1}cm^{-1}$ | $\epsilon^{Cl3-}$ $M^{-1}cm^{-1}$ |
|---|---|---|---|
| 220 | 69.89 | 57 | $1.04 \times 10^4$ |
| 232 | 100 | 0 | 8800 |
| 325 | 10.8 | 70 | 180 |

Solving these equations give the concentrations of the chlorine species. The experimental results are also shown in FIG. 5. As shown in FIG. 5, appreciable amount of $Cl_2$ begins to form at pH<3.5. In order to minimize the formation of $Cl_2$ gas, the pH of the solution should be controlled at 3.5 or higher. NVC-101 Solution Stability Experiments: The stability experiments were focused on measuring the total concentration of the active chlorine species. The experiments were carried out in ampules at 40° C., room temperature and 4° C. with an initial total active chlorine species concentration of 100 ppm (i.e. $[HOCl]_{total}=100$ ppm). The plots of $[HOCl]_{total}$ vs Time and pH vs time in FIG. 6 show that the HOCl at three temperatures is stable as determined by both $[HOCl]_{total}$, and by the pH of the solution. An initial drop in $[HOCl]_{total}$ is observed with samples taken within the first 2448 hours. This initial drop may be attributed to the loss of $Cl_2$ from the solution into the headspace. When the first data point was measured, the equilibrium as expressed in Eq. 14 had not been established. By the time the ampule was opened for analyzing the second data point after about 48 hours, the equilibrium in Eq. 14 was reached. Compared to the first data point, more $Cl_2$ in the solution had gone into the headspace of the ampule. After the initial drop in $[HOCl]_{total}$, no appreciable loss of HOCl was observed over 180 days. This experiment shows that HOCl is stable at pH 3.5 in a 0.9% NaCl solution after the equilibrium distribution of $Cl_2$ in solution and the gas phase was reached after about 48 hours.

Effect of Storage on the pH and ORP of the Solution in Screw Cap Bottles:

We conducted a study of the shelf life of the solution described according to the composition of Table 3 to determine the effect of extended storage in bottles made from various materials, and on the pH and oxidation-reduction potential (ORP) of the solution. Freshly prepared solution was stored over a period of 3 months in 4 types of screw cap bottle: The amber glass; the white (clear) glass; High Density PolyEthylene (HDPE); and TEFLON@). A variety of chemically non-reactive screw caps and liners were also tested. The stability and activity of the solution of the present invention may also be measured by determining the active halogen concentration using UV-VIS spectroscopy. For solutions containing active chlorine, the stability and activity of the solution of the present invention may also be measured by determining the active chlorine concentration using iodometric titration or using UV-VIS spectroscopy.

At given times over intervals of 5 to 10 days, known aliquots were withdrawn to measure the pH and ORP. Thirteen aliquots were taken over the testing period and each aliquots were measured for the pH and the ORP. At a starting pH of 2.8, the solutions stored in amber glass, white glass, HDPE, and in Teflon maintained a pH of 2.8 over a period of more than 75 days without change. It was also determined that containers using a Teflon liner that is backed by soft silicone was most effective in preventing the degassing of $Cl_2$ from the containers.

At a starting ORP value of 1175-1180, the solutions stored in amber glass, white glass, HDPE, and in Teflon maintained an ORP between 1150 and 1175 over a period of more than 75 days without a significant reduction in the ORP.

Stability of NVC-101 Solution in Sealed Ampules:

20 mL of the NVC-101 solutions prepared according to Procedure #1 was added via a dispenser to 25 mL glass ampules. The glass ampules were sealed immediately using a torch. The initial total concentration of active chlorine species of the solution was 2.69 mM (i.e. $[HOCl]_{total}$=2.69 mM) as measured by iodometric titration.

The ampules were stored at 40° C., at room temperature, and at 4° C. Individual ampules stored at the different temperatures were opened after 11 day, 15 days, 20 days, 29 days, 46 days, 62 days, 75 days, 103 days, 127 days, 180 days and analyzed for the total concentration of active chlorine species by iodometric titration. In addition, the pH of the solution was measured using a freshly calibrated Beckman pH meter.

A graphical plot (FIG. 6(a)) of the $[Chlorine]_{ppm}$ vs. time (in days) shows that the NVC-101 solutions at a pH of about 3.5 in a 0.9% NaCl solution prepared according to the methods described herein and stored in unreactive, sealed containers were stable at 40° C., at room temperature, and at 4° C. over a period of 180 days.

A graphical plot (FIG. 6(b)) of the pH of the solution vs. time (in days) shows that the NVC-101 solutions at an initial pH of about 3.5 in a 0.9% NaCl solution prepared according to the methods described herein and stored in unreactive, sealed containers were stable at 40° C., at room temperature, and at 4° C. over a period of 180 days.

The stability of a solution of this invention was investigated using different forms of packaging that would be practical for use by patients (Table 5). Sample A below represents the solution packaged in nine single-use 30 ml amber glass bottles with Teflon-lined screw caps and sealed with tape to ensure gas tightness. Sample B represents the same solution packaged in a 250 ml amber glass bottle and Sample C represents the same solution packaged in a 250 ml plastic bottle.

At the beginning of the experiment the concentration of free chlorine was measured. Each day (except for two weekend days) the following procedure was employed.

1. At the beginning of the day, the 250 ml bottles were opened for a period of two minutes and then closed.
2. At the end of the day, the 250 ml bottles were opened, a 20 ml sample was withdrawn and the bottle was closed after two minutes. The 20 ml samples were tested for free chlorine concentration.
3. At the end of the day one of the 30 ml bottles was opened and tested for free chlorine concentration. The bottle was then discarded.

TABLE 5

Stability of Solution over time in opened and closed containers $[HOCl]_{total}$ in ppm[a]

| Day | Closed container Sample A | Opened container Sample B | Opened container Sample C |
|---|---|---|---|
| 0 | 184 | 184 | 184 |
| 1 | 184 | 171 | 150 |
| 2 | 172 | 145 | 121 |
| 3 | 181 | 128 | 103 |
| 4 | — | — | — |
| 5 | — | — | — |
| 6 | 180 | 110 | 66 |
| 7 | 182 | 98 | 54 |
| 8 | 180 | 59 | 38 |
| 9 | 177 | 49 | 31 |
| 10 | 179 | 42 | 27 |

[a]$[HOCl]_{total}$ in ppm with a 5-10% experimental error.

The opening of the 250 ml bottles twice a day for two minutes was designed to reflect the pattern of usage of a normal patient, where the patient or a health care giver would be changing the dressing on the patients wounds and applying the solution twice a day.

It was surprisingly observed that the concentration of free chlorine and thus of hypochlorous acid was reduced very significantly over the period of the experiment when the larger bottles were repeatedly opened as described, whereas the single use bottles (30 ml) (Sample A in Table 5) maintained their concentration within acceptable levels. This indicates that each application of the solution of this invention should be from a container that has not been opened multiple times and preferably from a single-use container, such as a bottle.

In one aspect, the solutions of the present invention may be stored in single-use containers. In another aspect, the solutions of the invention may be stored in single-use containers of various different sizes, configurations, and having different volumes as suitable for the desired applications as disclosed herein. In some applications, for example, the solution of the invention may be stored in single-use 30 mL, optionally disposable containers.

Preparation of HOCl Solutions: In general, HOCl solutions were prepared by acidifying the NaOCl solution with HCl. The concentration of HOCl was determined by either Iodometric titration with Hatch solution or UV-VIS method. For analysis by UV-VIS method, aliquot of HOCl solution was converted to OCl⁻ (362 $M^{-1}cm^{-}$ @ 292 nm; see Furman, C. F.; Margerum, D. W. Inorg. Chem. 1998, 37, 4321) with 0.1 M NaOH solution. A Beckman pH meter was used to measure the pH of the solution.

Reagents. All solutions were made with Millipore water, which was validated with HPLC grade water. NaOCl (6%) solution was purchased from VWR. NaCl and HCl used are reagent-grade.

Procedure # 1: Preparation of NVC-101 Solutions

In a 500 mL Erlenmyer flask was placed NaCl (4.344 g). To this was added 450 mL of distilled water, followed by 1.6 ml of 0.6% NaOCl (VWR International), and 3.7 mL of 1 Molar hydrochloric acid. This solution was transferred to a 500 mL s volumetric flask and then enough distilled water was added to reach the 500 mL mark. ORP, pH, and total available chlorine were measured and recorded.

If sufficient acid is initially present in the solution to obtain the desired pH range, then no pH adjustment is needed. Otherwise, the pH may be adjusted to the desired range using standard methods known in the art for increasing or decreasing the pH of the aqueous solution.

In one example, when the physiologicaily-balanced, acidic solution of the invention is stored in a glass bottle, the composition has been shown to be stable for at least 90 days at room temperature.

Procedure #2: Preparation of 50 Liters of 1.70 mM HOCl Solution in 0.9% Saline at pH 3.5

The HOCl solution (1.70 mM) in 0.9% NaCl at pH 3.5 have been prepared in large scale using a 50-liter polyolefin plastic container as a reaction vessel. Table 6 lists the reagents and their quantity that may be used to obtain the desired concentration and pH value.

TABLE 6

| Reagent | MW (g/mole) | Weight (g) | mmoles | Volume (L) | Molarity (moles/liter) | Remarks |
|---|---|---|---|---|---|---|
| H$_2$O | 18 | | | 49.8 | | |
| NaCl | 58.5 | 440 | | | | 440 g makes a 0.9% solution in total volume of 50 liters |
| NaOCl | 74.5 | 92 | 1.70 | | 0.98 | |
| HCl | 36.5 | | 2.5 | 0.124 | 1.0 | |

In order to avoid losing active chlorine during the manufacturing of the solution, NaOCl was added in the last. An example of the manufacturing procedure for an HOCl solution in 0.9% saline at pH=3.5 is described as follows:

1. 440 g of NaCl was weighed in a 1000 mL-beaker, and then 500 mL Millipore water was added into the beaker to dissolve NaCl.
2. The solution was stirred for 5 minutes using a glass stir. About half of the NaCl remained undissolved. The NaCl solution was transferred into a 1000 mL volumetric flask. The undissolved NaGl solid was retained in the beaker.
3. The 1000 mL volumetric flask was filled with Millipore water up to the 1000 mL mark and the NaCl solution in the 1000 mL volumetric flask was transferred into the vessel.
4. Another 500 mL Millipore water was added into the 1000 mL beaker to dissolve the remaining NaCl solid. The solution was stirred until all NaCl dissolved. Repeat step 3.
5. 124 mL of 1.0 M HCl was pipetted into the 1000 mL volumetric flask. The flask was filled with Millipore water up to the 1000 mL mark. The HCl solution in the 1000 mL volumetric flask was transferred into the vessel.
6. The vessel was filled with Millipore water up to 47 liters, and the solution was stirred while the Millipore water was added.
7. 92 grams of NaOCl (6%) was weighed into a 500 mL beaker and the transferred into a 1000 mL volumetric flask and the flask was filled with Millipore water up to 1000 mL mark. The solution was transferred into the vessel. The volumetric flask was rinsed and filled up to the 1000 mL mark with Millipore water. The solution was transferred into the vessel.
8. The vessel was filled up to 50 liter.
9. The solution was stirred slowly and gently with a long glass stir bar for about 2 minutes.
10. After about 2 minutes, a test for the active chlorine concentration and pH of solution using UV-VIS method and pH meter, respectively, was made to determine if the solution has the desired concentration and pH.
11. The vessel was tightly capped. The solution was allowed to sit in the vessel for about 2 hours to reach equilibrium.
12. The concentration of HOCl and pH of solution are analyzed on UV-VIS spectrophotometer and pH meter before the solutions are added to containers such as ampules or bottles.

Using the manufacturing methods described above, the desired free chlorine concentration (1.70±0.05 mM) and pH (3.55±0.05) are consistently obtained.

An iodometric titration or UV-VIS method was used to determine the concentration of active chlorine species in solution.

Iodometric titration:

In an iodometric titration, the following reactions take place:

KI+HOCl→I$_2$+KCl

KI+Cl$_2$→I$_2$+KCl

KI+OCl$^-$→I$_2$+KCl

I$_2$+starch (used as an indicator)→Blue complex

I$_2$+2S$_2$O$_3^{2-}$→S$_4$O$_6^{2-}$+2 I$^-$ (end point is colorless)

The total concentration may be determined as [HOCl]$_{total}$=[HOCl]+[OCl$^-$]+[Cl$_2$]

Procedure for Iodometric Titration for Active Chlorine:

1. Set up titration apparatus using a HACH TetraStir™ apparatus as described by HACH Digital Titrator Manual.
2. Start with a clean 125-ml Erlenmeyer flask with a small stir bar in the flask.
3. Add the contents of 1 foil packet of Potassium Iodide Reagent (purchased from HACH) and one Dissolved Oxygen Powder Pillow (purchased from HACH) to flask.
4. Add Millipore water to the flask up to the 50-ml mark. Place flask on stir plate to completely dissolve the reagents.
5. Add 5 ml of sample test solution to the flask using an acclimated 5-ml pipet. Solution will turn yellow.
6. Ensure that there is sodium thiosulfate solution throughout the delivery tube, the counter is at zero, and the tip of the delivery tube is dry. Then begin titration.
7. Add sodium thiosulfate until the solution turns a very pale yellow. Then add 4-5 drops of starch indicator. The solution will turn blue.
8. Continue titration with sodium thiosulfate until the solution turns clear and remains clear for 30 seconds.

Using the above procedure for the analysis of NVC-101 solution in ampules, each data point reported is the average concentration of solutions analyzed from three ampules.

UV-VIS Method:

The solution to be tested is basified before it is measured by UV-VIS. Basification converts both HOCl and Cl$_2$ into a same species, OCl$^-$. OCl$^-$ has a strong absorbance at 292 nm, and therefore can provide a better signal and enhance the detecting limit.

Analysis using the UV-VIS method, the total concentration of the active chlorine species may be determined as [HOCl]$_{total}$=[HOCl]+[Cl$_2$]+[OCl$^-$].

HOCl+NaOH→NaOCl+H$_2$O

Cl$_2$+2NaOH→NaOCl+NaCl+H$_2$O

Procedure for Measurement of Active Chlorine by UV-VIS:

1. Pipet 10 ml of 0.1 M NaOH solution into a clean and dry 50-ml beaker.

2. Add 5 ml of NVC-101 test solution to this beaker. Mix with the NaOH solution well.

3. Use the basified NVC-101 solution to rinse the cell three times.

4. Fill the cell with basified NVC-101 solution and cap the cell.

5. Measure the OCl⁻ absorbance at 292 nm.

6. The total chlorine concentration may be calculated using the following equation:

$$[HOCl]_{Total} = 3 * (A_{292nm}/362)$$

where "3" is the dilution factor when the solution is basified, and "362 $M^{-1}cm^{-1}$" is the molar absorption of OCl⁻ at 292 nm.

Using the above procedure for the analysis of NVC-101 solution in ampules, each data point is the average concentration of the solutions from three ampules.

Antimicrobial Activity

Antimicrobial efficacy of a solution of the invention containing 9 g/L NaCl, 170 ppm. hypohalous acid, having a pH of 3.0 and an ORP of 1175 was tested against microorganisms including *Candida albicans*, spergillus niger, Streptococcos pnemonea, MRSA, VRE, Baccilus subtillis, Bacillis ceruis, Baccilus thorangensis, Baccilus anthracis, *Pseudomonas aeruginosa, Escherichia coli, Staphylococcus aureus, Listeria monocytogenes* 10403s wild type, catalase-deficient mutant *L. monocytogenes* LM1 370, *Aspergillus niger* (spores), *Penecillium oblatum* (spores), *Lactobacillus*, and *E. coli* 01 57:H7. Up to 5 logs of reduction in the activity of the microorganisms was achieved after 10 to 60 seconds of exposure to the solution of the present invention.

Antimicrobial properties: The solution of invention was effective in the treatment of all microorganisms, including gram positive, gram negative, yeast, fungi and spore forming Baccilus, including different strains of Baccilus anthracis. The solution was found to exert pronounced antibacterial action against all the microorganisms tested.

Eye and Skin Irritation

Eye Irritation Experiment

The solution of the invention was evaluated for primary ocular irritation based on the requirements of the International Organization for Standardization 10993: Biological Evaluation of Medical Devices, Part 10: Tests for Irritation and Sensitization.

A 0.1 ml dose of the solution of the invention was instilled into the lower conjunctiva sac of the right eye of the screen rabbit and the lid was gently closed for 1 second. The opposite eye was dosed with 0.1 ml of 0.9% sodium chloride (USP) as per sponsor to serve as the comparative control. The animal was returned to its cage following treatment. At 1, 24, 48, and 72 hours after dosing, the test eye of each rabbit was examined with an auxiliary light source for ocular irritation. Under the conditions of this study, the solution of the invention was not considered an irritant to the ocular tissue of the rabbit.

Skin Irritation Experiment

The solution of the invention was also evaluated for primary skin irritation based on the requirements of the International Organization for Standardization 10993: Biological Evaluation of Medical Devices, Part 10: Tests for Irritation and Sensitization. In cumulative skin irritation studies, two intact and two abraded skin sites were prepared on the skin on the back of each of six animals. Then, 0.5 mL of the solution of the present invention was applied to one intact skin site and one abraded skin site on each animal for 4 hours a day for a period of 5 days; 0.5 mL of distilled water was applied to the second intact skin site and the second abraded skin site on each animal for the same time period, as a control. No cumulative skin irritation effects were noted at the application sites of the solution of the invention compared to the distilled water.

We have studied the antimicrobial properties of the solutions of the present invention as well as the behavior of these solutions with respect to eye and skin irritation and find the following results:

Skin irritation index of the solution of invention was zero as it was compared to sterile saline.

Eye irritation index of the solution of invention was also zero as it was compared to sterile saline.

IV. Methods for Using the Composition of the Invention

Application of the stable aqueous physiologically-balanced, non-cytotoxic ionized acidic solution of the present invention, has been demonstrated to help wound healing progress remarkably. Antimicrobial properties of acidic salt solutions of the invention are such that they enhance the healing process of any wound contaminated with microorganisms. The compositions of the invention function specifically to maintain the necessary antimicrobial environment for wounds to heal faster, without the usual complications associated with superficial infections. In addition, the solutions provide topical microbial control and humidification of chronic wounds.

The use of acidic salt solutions of the present invention has been instrumental in healing a number of patients with deep wounds which were not responding to usual medications and locally applied treatments. In one aspect, the present invention provides a method for the treatment of various medical conditions such as promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis and related diseases, treatment of viral infections, treatment of skin diseases, and tissue repair and regeneration, which method comprises using the solution of the present invention by applying the solution to the site where treatment is required. Non-limiting examples of biofilm that may be treated using the solutions of the present invention include those cited in the review article entitled "Is there a role for quorum signals in bacterial biofilms?" by S. Kjelleberg, and S. Molin, PMID: 12057677 (PubMed-indexed for MEDLINE).

The physiologically balanced, solutions of the invention may be effective in reducing bacterial load thus improving wound healing. Preliminary product development studies in human patients with chronic wounds suggest that solutions are well tolerated, improve the granulation of wound tissue, reduce the need for debridement compared to prior art solutions with patients reporting less pain during their treatment. In addition, preliminary product development studies suggest that, when solutions are applied to patients with artificial skin grafts that are infected and normally need surgical replacement of the graft, the infections are eliminated and the grafts are saved.

Three recent case studies involving the treatment of human subjects with a preferred composition of the invention are presented below. In these case studies, the acidic salt solution was essentially the same as that described for the solution in Table 2. This composition provides osmolarity compatible with blood plasma. The wounds were kept continuously moist with the composition of the invention, and were covered with Vaseline gauze to prevent evaporation of the solution.

Case Study #1

The patient was a 70 year-old female, with a long history of severe venous edema, lymphaedema, and obesity. Her vascular supply was normal. She developed a cutaneous ulcer 2 years ago in the lower right leg. A second ulcer subsequently developed in the lateral right leg. The ulcers had previously been treated using multiple methods, including debridement, antibiotics, topical solutions including BETADINE® (Purdue Frederick, Norwalk, Conn.); SILVADINEO (BASF Corporation, Mt. Olive, N.J.); ELASE® (Fujisawa Co., Deerfield, Ill.); and FURACIN® (Roberts Pharmaceutical Corp., Meridian Center, Ill.). By way of explanation, BETADINE® is an antiseptic cleanser, used externally on wounds; an iodine-containing preparation used as a broad spectrum antimicrobial. SILVADINE® is a soft white cream containing 1% silver sulfadiazine antimicrobial agent which is applied to wounds after cleaning and debriding. ELASE® is an enzymatic powder or cream used as a debridement agent in wounds where circulation is poor, to destroy dead tissue and leave healthy tissue intact. FURACIN® is a nitrofurazone broad-spectrum antibacterial cream used against pathogens commonly causing surface infections. Use of these agents in the wound healing had not produced the desired results.

A biopsy revealed benign ulceration and granulation tissue. The possibility of Pyodermo Gangrenosum was considered. The initial measurements of these severely necrotic ulcers were 130×180 mm and 98×125 mm. Treatment included bedrest, debridement, antibiotics, and topical application of the composition of the invention made according to experimental detailed previously in Example #1, for hydration and topical bacterial control. Within 10 days, the ulcers were almost completely covered with crisp red granulation tissue and the pain was gone. Within 14 days, a split thickness skin graft closed the wound; the patient was able to leave the hospital 8 days later. Within two months following the start of treatment, the ulcers had completely healed, and the patient remained pain-free.

Case Study #2

The patient was a 50 year-old male, with a history of thrombophlebitis, pulmonary emboli, and obesity. The patient had experienced infected hematomatous ulceration in both groins and bilateral venous ulcers in both legs for several months. He had an antithrombin III deficiency and had been coumadinized. By way of explanation, Antithrombin III is a protein consisting of normal plasma and extracellular sites that inactivates thrombin in a time-dependent irreversible reaction and serves as a cofactor of heparin into its anticoagulant activities. Antithrombin III also inhibits certain coagulation factors-occurs in certain disease process i.e., liver disease or may be genetic. Coumadinized refers to the use of crystalline warfarin tabs or Heparin i.V. Anticoagulant to treat patients who have thrombosis to prevent further thrombus. COUMADINE® is manufactured by DuPont® Pharmaceutical, Wilmington, Del. Because of the recent hemorrhages in his groin, he developed large deep ulcerations on the right (measuring 140×90 mm) and more superficial ulcerations on the left (50×50 mm and 60×60 mm). After the first debridement of infected necrotic fat, the culture revealed the presence of vancomycin-resistant *Enterococcus*. Treatment consisting of topical application of the composition of the invention was started. Infectious disease consultation recommended no further antibiotic treatment. Topical dressings consisting of sponges soaked with the composition of the invention were packed into the wound and the patient was subjected to bedrest. The distal venous ulcers healed fairly rapidly and required only two more debridements. The left groin ulcer undermined and required opening further while the packing was soaked with the composition of the invention. The patient then began healing, with good granulation tissue forming and epidermal coverage to 90% in the right groin ulcer. The left groin ulcer required debridement for undermining, but began healing without antibiotic treatment.

Case Study #3

The patient was a 57 year-old male, who had experienced recurrent ulcers of both feet and ankles over the past four years. Local wound care had initially been started by coagulating veins and using topical wound therapy. His UNNA® boots caused an increase in his ulcerations, which then became more severe. By way of explanation, an UNNA® boot is an elastic adhesive bandage applied over zinc oxide cream as a protective treatment. An UNNA® boot is a boot-like dressing of the lower extremity made of layers of gauze and UNNA® 's paste; 100% soft cotton gauze impregnated with non-hardening zinc oxide paste. The manufacturer of UNNA®'s paste is Glenwood, Inc. of Tenalty, N.J. He had been using a JOBST® pump for edema control. This pump is designed for intermittent home use and is connected to an inflatable pneumatic appliance which is typically preset to alternate 90 seconds of inflation with 30 seconds of deflation. The manufacturer of JOBST® pumps is Nutech, of San Antonio, Tex.

At the time we examined the patient, his wound measurements were 33×65×2 mm, 17×25×2 mm, and 5×9×2 mm. Physical evaluation verified excellent pulsatile inflow to the leg; the wounds were therefore diagnosed as venous ulcers because of the significant edema present. The patient began compression therapy and debridement, culturing the leg at the same time; the bacteria present were found to be coagulase-negative, methicillin-resistant *Staphylococcus* and *Enterococcus* sensitive to vancomycin. He also had *Haemophilus* and diphtheroids cultured with polymicrobial infection. The patient had persistent nonhealing 10 infections for several months, and the infections had become resistant to the classic antibiotic treatments. The infections were only sensitive to CIPROFLOXACIN® and BACTRIM DS®. CIPROFLOXACIN® is a broad spectrum antibiotic, manufactured by Miles Pharmaceutical, West Haven, Conn., which is active on Gram+ and Gram-bacteria, and is typically used to treat skin, bone and joint infections. BACTRIM DS® is manufactured by Roche of Nutley, N.J. BACTRIM DS® is a sulfonamide antibiotic, which is typically used to treat urinary tract infections, and is also used to treat *E. coli, Proteus* species, Shegellosis and Pneumocystic pneumonia infections. The patient was started on CIPROFLOXACIN®, which was then discontinued, and then BACTRIM DS® was started. He had topical debridements.

Since no significant improvement was shown after the treatment described above, topical application of the composition of the invention was begun for control of the bacteria and hydration. The infections were rapidly controlled after the start of treatment with the composition of the invention, and the wounds began healing fairly rapidly. He has now shown healing of the two ulcers, with the final measurements down to 7×41 mm and 7×11 mm on the right medial and lateral ankle, respectively.

Oral Care

The physiologically-balanced, acidic solution of the invention may be used to treat canker sores (mouth ulcers) or cold sores by rinsing the affected area. The solution can be used by soaking the cold sore 3-4 times a day, each time with 2-3 applications, and putting the solution in contact with the sore for 20-30 seconds. The solution may also be used as a mouth rinse for dental and mouth hygiene and to control infection. In this instance, the solution may be used as a gargling solution to fight throat infection. The solution may be applied with the help of a cotton swab for more specific areas. The solution can be used once or several times a day according to patient's needs and condition.

Ophthalmic Care

The physiologically-balanced, acidic solution of the invention may be used in place of a saline solution to remove a foreign body from, to rinse, or to irrigate the eyes. It can also be applied topically before or after surgery to disinfect an eye and surrounding tissues. Our studies on rabbits eyes showed that this solution is as safe as saline solution when applied to rabbits' eyes and has no toxicity to the eyes when compared to ophthalmic grade BETADINE® (5%) typically used pre-surgery. The solution can be used once or several times a day according to a patient's needs and condition. The solution can be applied by dropping it directly into the eyes as necessary. It can also be applied by soaking a gauze and applying the saturated gauze to the eyes for 1 or several minutes. It can also be used to clean the eyes by gently wiping the eyes with a saturated gauze. The solution can also be poured into a small eye washer, then the washer is inverted over the eye washer and the eyelid opened and closed several times.

The stable, physiologically-balanced, acidic solution of the invention may be used for the treatment of ocular disinfection or decontamination. In addition, it may be used as a replacement for silver nitrate in the disinfection of the eyes of neonates. The reader will see that the solution of the invention has applications in the treatment of many different types of wounds, including, without limitation, diabetic ulcers, gangrene, venous ulcers, decubitus ulcers, pressure ulcers, wounds due to bites, acute trauma wounds, surgical wounds and burns. The composition of the invention is also useful as an irrigation solution, for example, during dental, periodontal, and ophthalmic procedures. The composition of the invention can also be used for pre- and post-operative cleaning of tissue sites, and as a gargling solution for treatment of canker sores. In addition, the HOCl contained in the solution may stimulate or enhance growth factors essential for the wound healing process. As such, the solution may find uses in many other applications in which disinfection and growth factor stimulation are desirable.

Methods of Using Solution for Skin Disinfection:

The solution of the present invention may also be used to treat skin that are infected. In a skin of a patient showing medical signs of infection, the solution of the present invention may be applied directly to the area of the skin that are infected. After at least one application of the solution onto the infected skin using standard methods of application known in the art, the disinfection properties of the solution maybe noted.

Reduction of Pathogens in Pulmonary Infections:

The solution of the present invention may be used for the reduction of pathogens in pulmonary infections. For example, various viral or bacterial infections may be effectively treated with the solution of the present invention. Non-limited examples of infections that may be effectively treated using the solution of the present invention include anthrax spores present in the lungs, and the reduction of pneumonia causing bacteria in the lungs, including strep bacteria and the like.

Method of Using the Solution of Invention for Cleaning Eyes in Pediatrics:

The solution of the present invention may be used for the cleaning eyes in adults and in pediatrics. For example, various viral infection, bacterial infections, or pathogenic agents may be effectively treated with the solution of the present invention. Non-limiting examples of pathogenic agents that have been successfully treated with the solution of the present invention include *chlamydia trachomatis*, gonorrhea as well as other viral infections.

Method of Using the Solution of Invention in Gynecology:

The solution of the present invention may be used for the treatment of 10 gynecological infections, such as urinary tract infections and the like. For example, various microorganisms, yeasts (e.g., Monilia, *Candida albicans*, etc. . . . ), bacterial infections, HSV-2 or other pathogenic agents may be effectively treated with the solution of the present invention. Optionally, the application of the solutions of the present invention can be used with other medications for the treatment of gynecological infections.

Method of Wound Care:

Patients suffering from long-lasting non-healing wounds should be treated with the physiologically-balanced, acidic solution of the present invention on a daily basis, typically about twice a day. The solution of the invention, for example, having a concentration of about 180 ppm of total active chlorine and a pH of 2.5 may be used in place of a saline solution, to control infection and to help the wound healing mechanisms. The solution of the invention may be used as follows: a gauze material or gauze pad is presoaked with enough solution to saturate it and is then squeezed to remove excess solution. This removes species present in the gauze which would react with and reduce the effectiveness of the solution of the invention. The gauze is wetted after this procedure, but not soaked. Additional solution is then applied to completely wet the gauze, which is then immediately applied to the wound. In the alternative, the gauze may be applied to the wound and then additional solution applied. Typically the wound site is packed with the solution-soaked gauze, and optionally, a Vaseline gauze can be applied on top of the packed wound to keep it moist and free of contaminating germs. The wound site is then wrapped with wound dressings as is standard in the art. The solution may also be used to clean a wound by pouring it directly on the wound site to remove any necrotic tissue by a mechanical procedure, and also as a cleanser or irrigant.

The patient may also make use of a "wound care kit" which permits the patient to periodically pour the solution of the present invention onto the wound site without having to remove the dressing. This kit provides ease-of-use, portability and dramatically reduce exposure of the wound. The wound care kit includes a package containing the solution of the invention and bandaging material. Preferably the kit contains a package containing the solution of the invention and a specialized bandage for use in combination with the solution. The specialized bandage keeps the skin surrounding the wound dry while the wound is treated. Further, the bandage may be applied in a physician's office or at a hospital, with the patient continuing care at home; may be applied and used at home under the instructions of a physician; or for minor injuries, the wound care kit may be used as an "over the counter" treatment by the patient alone.

In another aspect of the invention, the solutions of the present invention may be packaged to contain the solution in individual, single use containers. The single-use containers may be used for example, for application in single change of dressing or equivalents thereof. The single-use containers of the present invention may be used in conjunction with the specialized bandages disclosed in the present invention. In another aspect of the invention, a wound care kit may comprise single-use containers of the solutions of the present invention with the specialized bandages for various applications disclosed herein.

IV. Description of the Wound Care Kit

The wound care kit includes bandaging material and a package of the solution of the invention. Preferably the packaging material provides the kind of non-reactive (with the solution) surface previously described herein. In addition, the bandaging material preferably includes a specially designed wound "bandage" made out of an oxygen-permeable bandage material to prevent the wounded tissue from drying. FIGS. 2A-2C and FIG. 3 describe the bandage and illustrate the use of the bandage on a wound surface, respectively. The bandage is described in more detail subsequently. The kit may also include gauze or a similar material for packing of the wound, to be used in combination with the solution and a bandage.

V. Description of the Specialized Bandage

The specialized bandage of the present invention comprises an opening, which may also be described as a "window" through which the solution of the invention or other topical material may be applied periodically as needed depending on the indication. Preferably, the bandage includes a dew/moisture sensor, an electrically-conductive sensor which measures ion content, or other bandage property sensor which provides an indication of the status of the bandage related to treatment of the wound. For example, and not by way of limitation, a dew/moisture indicator which provides a colored indication when the bandage solution content has become low, or a signal-producing device such as a sound indicator or an electrical signal output indicator when the ion content of the treatment solution has become low so that the bandage is no longer sufficiently effective.

Figure 2A:
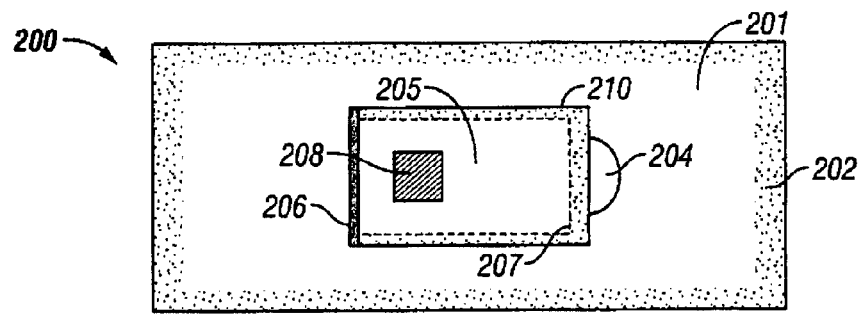
FIG. 2A is a schematic top view of an air-permeable bandage 200, including outer portion 201 having a primary adhesive border 202; an inner portion 210 including a lifting flap 205 having a secondary adhesive border 207, a lifting tab 204, which assists in the lifting of flap 205, a hinge 206, and a dew/humidity indicator 208 (or other sensor/indicator as will be described subsequently herein).
Figure 2B:
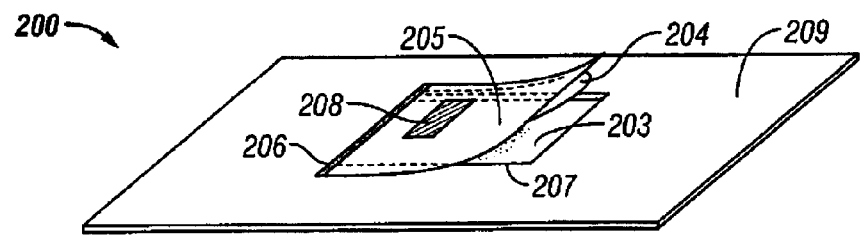
FIG. 2B is a schematic side view of air-permeable bandage 200, showing lifting flap 205 and lifting tab 204 in a partially lifted position, to provide a window opening 203 through bandage 200. A portion of secondary adhesive border 207 has been lifted above the upper surface 209 of bandage 200.
Figure 2C:
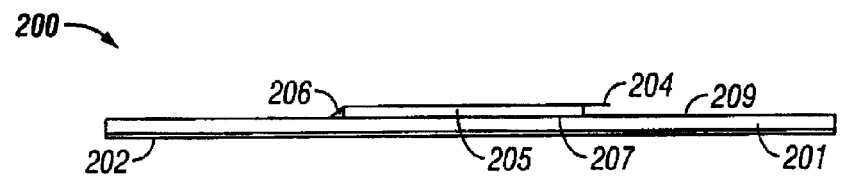
FIG. 2C is a schematic cross-sectional view of air-permeable bandage 200, with lifting flap 205 and lifting tab 204 in a lowered position, secured to upper surface 209 of bandage 200 by secondary adhesive border 207.

One embodiment of the bandage invention is shown in FIGS. 2A-2C, The bandage 200 includes an outer portion 201 having a primary adhesive border 202; an inner portion 210 including a lifting flap 205 having a secondary adhesive border 207, a lifting tab 204, which assists in the lifting of flap 205, and a hinge 206. Optionally the bandage has a dew/humidity indicator 208, or an electrically-conductive sensor, where the sensor may be attached to a signal generator, which occupies a position within inner portion 210 of bandage 200. FIG. 2B is a schematic side view of air-permeable bandage 200, showing lifting flap 205 and lifting tab 204 in a partially lifted position, to provide a window opening 203 through bandage 200. A portion of secondary adhesive border 207 has been lifted above the upper surface 209 of bandage 200. FIG. 2C is a schematic cross-sectional view of air-permeable bandage 200, with lifting flap 205 and lifting tab 204 in a lowered position, secured to upper surface 209 of bandage 200 by secondary adhesive border 207. One skilled in the art can envision a number of similar designs which will accomplish the function and utility of the bandage in a similar manner, and such designs are considered to be included in the present invention.

Figure 3:
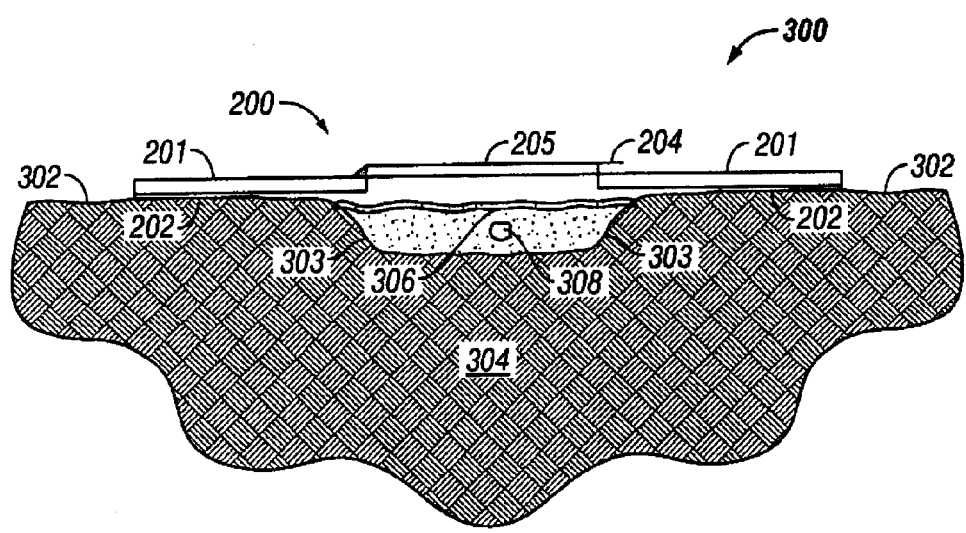
FIG. 3 is a schematic cross-sectional view 300 of an air-permeable bandage 200 of the kind shown in FIGS. 2A-2C, applied over a subcutaneous wound 303. The subcutaneous tissue 304 is packed with gauze 306 which has been soaked in the physiologically balanced, electrolyzed, acidic solution 308 of the present invention. The bandage 200 is adhered to the skin surface 302 by a primary adhesive border 202. Bandage lifting flap 205 can be lifted via tab 204 to expose gauze 306 for the application of additional solution 308 when a dew/humidity indicator (not shown) or other sensing/indication device (not shown) indicates a low level of humidity of the gauze 306.

FIG. 3 is a schematic cross-sectional view 300 of an air-permeable bandage 200 of the kind shown in FIGS. 2A-2C, applied over a subcutaneous wound 303. The subcutaneous tissue 304 is packed with a packing material 306 such as gauze, which has been treated to reduce or eliminate reactivity with oxidants and then soaked in the physiologically balanced, electrolyzed, acidic solution 308 of the present invention. The bandage 200 is adhered to the skin surface 302 by a primary adhesive border 202. Bandage lifting flap 205 can be lifted via tab 204 to expose packing material 306 for the application of additional solution 308 when desired. A dew/humidity indicator (not shown), or electrically-conductive indicator (not shown) may be used to indicate the appropriate time for addition of solution 308.

In another aspect of the bandage invention, the window may have no permanent connecting hinge with the bandage and may be removably attached or secured to the bandage by various connecting or attaching means known in the art. Non-limiting examples of such connecting or attaching means include Velcro attachments, removable adhesives or tacking surfaces. The removable windows in the bandages of the present invention permit the changing or replacement of the windows without the need for replacing the entire outer bandage.

In another aspect of the bandage invention, individual bandages of variable sizes and configurations may be supplied and sold separately with the corresponding detachable windows of particular sizes and configurations that may accommodate the bandage. Optionally, the windows may be designed such that the windows properly overlaps with the bandage such that the windows fully cover the wounds and have overlapping surfaces with the bandage such that the windows may be securely attached to the bandage.

The bandage provides ease-of-use to the patient by allowing the patient to pour the solution onto his wound or onto wound packing without having to remove the entire dressing. A more complicated version of the bandage, such as one having an electrically-conductive sensor which may be connected to monitoring equipment is particularly helpful in a hospital setting.

In another aspect of the bandage invention, the bandages of variable sizes, contours and shapes may be pre-fabricated with perforated outlines of one or more windows of variable sizes, dimensions and configurations such that the bandage may be adapted or custom fitted to the size, shape and configuration of the wounds. The bandages maybe designed for variable sizes, shapes, and contours that can be made to accommodate the specific anatomical dimensions of the body. Particular areas of the body that may require specially designed bandages include various joints, the elbows, knees, fingers and toes, and other locations of the human anatomy having non-flat surfaces or curves.

The perforations in the bandages allows a health caregiver or the patient to use a generically manufactured, perforated bandage to manually remove the inner window of the bandage by cutting or tearing along the perforations defining or outlining a window that custom matches the size, shape or configuration of the wound. In addition, the perforations permit the application of a single bandage for application to wounds of various sizes and dimensions, and permit medical facilities and suppliers to stock only a small number of intermediate sizes of bandages that may accommodate wounds of various sizes and configurations.

Aspects of the Invention:

In one aspect of the invention, there is provided a stable aqueous physiologically balanced, ionized solution comprising: (a) an acidic solution of hypohalous acid with a concentration from about 10 ppm to about 200 ppm; (b) a halide comprising salt, from about 0.4 g/L to about 20.4 glL, said solution having a pH range from about 3.0 to about 4.0, and (c) said solution when stored in a chemically non-reactive container at room temperature over at least three months, the solution is characterized as having a reduced hypohalous acid concentration of between 1-95% as determined by UV-VIS or by iodometric titration.

In another aspect of the invention, the solution is further characterized as having a pH range from about 3.5 to about 4.0. In another aspect, the stable solution has a pH of about 3.5.

In another aspect, the solution is further characterized as capable of being stored in a chemically non-reactive container at room temperature over at least three months, the solution is characterized as having a reduced hypohalous acid concentration of between 0-5% as determined by UV-VIS or by iodometric titration.

In yet another aspect, the stable solution may be stored in a chemically non-reactive container at room temperature over at least three months, the solution is characterized as having a reduced hypohalous acid concentration of between 5-15% as determined by UV-VIS or by iodometric titration.

In another aspect of the invention, the hypohalous acid comprises the active chlorine species HOCl, NaOCl, and $Cl_2$, and the pH of the solution is about 3.5.

In one aspect of the invention, there is provided a stable aqueous physiologically balanced, ionized solution, wherein the chemically non-reactive container is a gas-tight, sealed container is made from material that is non-permeable and resistant to oxidative degradation.

In another aspect, the chemically non-reactive container is a gas-tight, sealed container made from PFA or equivalent PFA compositions or Teflon compositions. In another aspect, the container is non-permeable to the species of the NVC-101 solution.

In yet another aspect, the stable solution is further characterized as having an original oxidation reduction potential (ORP) at room temperature ranging from about +600 mV to about +1200 mV, and said ORP ranging from no less than about 90 to 97.5% of the original ORP after three months at room temperature.

In one aspect, the hypohalous acid is selected from the group consisting of HOBr, HOI, HOCl, and HOF. In another aspect, the hypohalous acid concentration is from about 40 to about 190 ppm.

In yet another aspect, the halide comprising salt is a member selected from the group consisting of lithium, sodium, potassium, magnesium, zinc, cesium, rubidium, and barium halide.

In yet another aspect, the halide comprising salt is a single salt. In yet another aspect, the hypohalous acid concentration of the stable solution is measured by iodometric titration or UV-VIS spectroscopy.

In another aspect, the chemically non-reactive container is designed for single use or single application packaging.

In a further aspect, there is provided a stable aqueous physiologically balanced, ionized solution comprising: (a) an acidic solution of hypochlorous acid (HOCl) with a concentration, from about 10 ppm to about 200 ppm; (b) a chloride comprising salt, from about 0.4 g/L to about 16 g/L, said solution having a pH range from about 3.5 to about 4.0, and (c) said solution when being stored in a chemically non-reactive, single use container at room temperature over at least three months and having a reduced hypochlorous acid concentration of between 1-95% as determined by UV-VIS or by iodometric titration.

In one aspect, the container is a single use PFA lined container.

In one aspect, there is provided a method for the treatment of various medical conditions selected from the groups consisting of promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using a solution of the invention by applying the solution to the site where treatment is required.

In yet another aspect, there is provided a method for the treatment of various medical conditions selected from the groups consisting of promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using a solution of the invention by applying the solution to the site where treatment is required.

In another aspect, the solution is characterized as having an original oxidation reduction potential (ORP) at room temperature ranging from about +600 mV to about +1200 mV, and said ORP ranging from no less than about 90 to 97.5% of the original ORP after at least three months at room temperature.

In a further aspect, there is provided a solution wherein the hypochlorous acid concentration is from about 40 to about 190 ppm. In another aspect, the chloride comprising salt is a member selected from the group consisting of lithium, sodium, potassium, magnesium, zinc, cesium, rubidium, and barium chloride. In yet another aspect, the chloride comprising salt is a single salt.

In another aspect, there is provided a solution wherein the pH ranges from about 3.5 to about 4.0. In another variation of the solution, the chloride comprising salt is sodium chloride. In one aspect, the concentration of sodium chloride is from about 4 g/L to about 9 g/L.

In one aspect of the invention, the molar ratio range of $OCl^-$ over the sum of $OCl^-$ and HOCl at 20° C. is about 0 to about 0.26%.

In another aspect, there is provided a method for the treatment of various medical conditions selected from the groups consisting of promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using a solution of the invention by applying the solution to the site where treatment is required.

In one aspect, there is provided a process for the preparation of a solution of the invention, wherein the solution is prepared by chemical methods, including chemical synthesis, mechanical methods such as by mixing, electrolysis or prepared in situ.

In another aspect, the halide comprising salt solution is converted to an acidic solution by electrolysis.

In yet another aspect for the process for preparing a solution of the invention, the pH of the solution is adjusted to about 3.5 to about 4.0. In yet another aspect, the solution is prepared by chemical synthesis comprising of the following reactions:

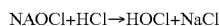

wherein the concentration of NaOCl in solution is about 2.5 mmol/L and the concentration of HCl is about 7.4 mmol/L, the resulting solution is adjusted to a pH of about 3.5 to about 4.0, and the solution is allowed to reach equilibrium without agitation for at least 2 hours.

In another aspect, there is provided a process wherein the solution is prepared in situ by mixing chemicals to form the stable aqueous physiologically balanced, non-cytotoxic ionized solution at the site of the tissue in need of treatment.

In yet another aspect, there is provided a method of promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, or a combination thereof, by treating a patient in need of such therapy with an effective amount of a stable, physiologically-balanced, acidic composition comprising an aqueous stable solution of the present invention. In a further aspect, there is provided the above method that comprises a) exposing area of damaged tissue; b) applying the solution to dermal tissue; c) irrigation of damaged tissue using the solution; and d) cleaning or treating tissue using the solution.

Accordingly, the above described preferred embodiments are not intended to limit the scope of the present invention, as one skilled in the art can, in view of the present disclosure, expand such embodiments to correspond with the subject matter of the invention claimed below.

The invention claimed is:

1. A method for the treatment of a medical condition selected from the groups consisting of disinfection or decontamination of open wounds and burns, promotion of wound healing, and ocular disinfection or decontamination in a patient in need of such treatment comprising: applying to a treatment site with an effective amount of a stable aqueous physiologically balanced, ionized solution comprising an acidic solution of hypohalous acid with a concentration from about 10 ppm to about 200 ppm; a halide comprising salt, from about 0.4 g/L to about 20.4 g/L, said solution having a pH range from about 3.0 to about 4.0, an original oxidation reduction potential (ORP) at room temperature ranging from about +600 mV to about +1200 mV, and said ORP ranging from no less than about 90 to 97.5% of the original ORP after three months at room temperature; and said solution when stored in a chemically non-reactive container at room temperature over at least three months, the solution is characterized as having a reduced hypohalous acid concentration of between 1-95% as determined by UV-VIS or by iodometric titration.

2. A method for the treatment of a medical condition selected from the groups consisting of disinfection or decontamination of open wounds and burns, promotion of wound healing, and ocular disinfection or decontamination in a patient in need of such treatment comprising: applying to a treatment site with an effective amount of a stable aqueous physiologically balanced, ionized solution comprising an acidic solution of hypohalous acid with a concentration from about 10 ppm to about 200 ppm; a halide comprising salt, from about 0.4 g/L to about 20.4 g/L, said solution having a pH range from about 3.5 to about 4.0, an original oxidation reduction potential (ORP) at room temperature ranging from about +600 mV to about +1200 mV, and said ORP ranging from no less than about 90 to 97.5% of the original ORP after three months at room temperature; and said solution when stored in a chemically non-reactive container at room temperature over at least three months, the solution is characterized as having a reduced hypohalous acid concentration of between 1-95% as determined by UV-VIS or by iodometric titration.

3. A method of disinfecting or decontaminating open wounds and burns, promoting wound healing, or disinfecting or decontaminating in or around the eye, by treating a patient in need thereof with an effective amount of a stable aqueous physiologically balanced, ionized solution comprising an acidic solution of hypohalous acid with a concentration from about 10 ppm to about 200 ppm; a halide comprising salt, from about 0.4 g/L to about 20.4 g/L, said solution having a pH range from about 3.0 to about 4.0, an original oxidation reduction potential (ORP) at room temperature ranging from about +600 mV to about +1200 mV, and said ORP ranging from no less than about 90 to 97.5% of the original ORP after three months at room temperature; and said solution when stored in a chemically non-reactive container at room temperature over at least three months, the solution is characterized as having a reduced hypohalous acid concentration of between 1-95% as determined by UV-VIS or by iodometric titration.

4. The method of claim 3, comprising:
a) exposing area of damaged tissue;
b) applying the solution to dermal tissue;
c) irrigation of damaged tissue using the solution; and
d) cleaning or treating tissue using the solution.

5. The method of claim 1, wherein the halide comprising salt is in concentration from about 4 g/L to about 10 g/L.

6. The method of claim 1, wherein the hypohalous acid is selected from the group consisting of HOBr, HOI, HOCl and HOF.

7. The method of claim 1, wherein the halide comprising salt is selected from the group consisting of lithium, sodium, potassium, magnesium, zinc, cesium, and barium halide.

* * * * *